(12) United States Patent
Gomez-Rios et al.

(10) Patent No.: US 12,362,163 B2
(45) Date of Patent: Jul. 15, 2025

(54) MOLECULAR CRYPTOGRAPHIC SAMPLING DEVICES AND METHODS OF MAKING AND USING

(71) Applicant: RESTEK CORPORATION, Bellefonte, PA (US)

(72) Inventors: German A. Gomez-Rios, Bellefonte, PA (US); Thomas E. Kane, Bellefonte, PA (US); Tracey A. Peters, Bellefonte, PA (US)

(73) Assignee: RESTEK CORPORATION, Bellefonte, PA (US)

( * ) Notice: Subject to any disclaimer, the term of this patent is extended or adjusted under 35 U.S.C. 154(b) by 834 days.

(21) Appl. No.: 17/597,611

(22) PCT Filed: Jul. 16, 2020

(86) PCT No.: PCT/US2020/042373
§ 371 (c)(1),
(2) Date: Jan. 13, 2022

(87) PCT Pub. No.: WO2021/011797
PCT Pub. Date: Jan. 21, 2021

(65) Prior Publication Data
US 2022/0293411 A1    Sep. 15, 2022

Related U.S. Application Data

(60) Provisional application No. 62/874,763, filed on Jul. 16, 2019.

(51) Int. Cl.
*B01L 3/00*    (2006.01)
*B01F 33/302*    (2022.01)
(Continued)

(52) U.S. Cl.
CPC ...... *H01J 49/165* (2013.01); *B01L 3/502715* (2013.01); *G01N 33/94* (2013.01);
(Continued)

(58) Field of Classification Search
CPC .... H01J 49/165; H01J 49/4205; H01J 49/167; H01J 49/0409; B01L 3/502715;
(Continued)

(56) References Cited

U.S. PATENT DOCUMENTS 9,082,600 B1 *  7/2015  Greving ............... B01L 3/5088
9,733,234 B2    8/2017  Pauliszyn et al.
(Continued)

*Primary Examiner* — Jennifer Wecker
*Assistant Examiner* — Oyeleye Alexander Alabi
(74) *Attorney, Agent, or Firm* — McNees Wallace & Nurick LLC

(57) ABSTRACT

A molecular cryptographic sampling device is disclosed including at least one unique identifying indicia disposed on the molecular cryptographic sampling device, a substrate including at least one depression disposed in or protrusion disposed on a surface of the substrate, at least one polymeric sorbent coating disposed on the at least one depression or protrusion, and at least one molecular encrypted code disposed on the at least one polymeric sorbent coating. The at least one molecular encrypted code includes at least one molecular tag, wherein the at least one molecular encrypted code is uniquely associated with the at least one unique identifying indicia in a database or by a predetermined algorithm.

20 Claims, 30 Drawing Sheets

(51) Int. Cl.
| | |
|---|---|
| B01F 33/3033 | (2022.01) |
| B01L 7/00 | (2006.01) |
| B01L 9/00 | (2006.01) |
| B23D 63/00 | (2006.01) |
| B29C 37/00 | (2006.01) |
| B65G 47/80 | (2006.01) |
| B82Y 15/00 | (2011.01) |
| B82Y 20/00 | (2011.01) |
| B82Y 30/00 | (2011.01) |
| B82Y 40/00 | (2011.01) |
| C12M 1/34 | (2006.01) |
| C12M 3/06 | (2006.01) |
| C12N 1/14 | (2006.01) |
| C12N 1/20 | (2006.01) |
| C12Q 1/02 | (2006.01) |
| C12Q 1/6806 | (2018.01) |
| C12Q 1/6844 | (2018.01) |
| C12Q 1/6848 | (2018.01) |
| C12Q 1/686 | (2018.01) |
| C23C 2/00 | (2006.01) |
| G01N 1/40 | (2006.01) |
| G01N 15/10 | (2024.01) |
| G01N 15/14 | (2024.01) |
| G01N 15/1433 | (2024.01) |
| G01N 21/29 | (2006.01) |
| G01N 21/41 | (2006.01) |
| G01N 21/45 | (2006.01) |
| G01N 21/65 | (2006.01) |
| G01N 27/04 | (2006.01) |
| G01N 27/12 | (2006.01) |
| G01N 33/00 | (2006.01) |
| G01N 33/543 | (2006.01) |
| G01N 33/574 | (2006.01) |
| G01N 33/58 | (2006.01) |
| G01N 33/94 | (2006.01) |
| G01N 35/10 | (2006.01) |
| G02B 6/42 | (2006.01) |
| H01J 49/16 | (2006.01) |
| H01J 49/42 | (2006.01) |
| H04L 9/32 | (2006.01) |

(52) U.S. Cl.
CPC ...... G01N 35/1009 (2013.01); H01J 49/4205 (2013.01); H04L 9/32 (2013.01); *B01L 2300/0654* (2013.01); *B01L 2300/069* (2013.01)

(58) Field of Classification Search
CPC ....... B01L 2300/0654; B01L 2300/069; B01L 2200/141; B01L 2200/148; B01L 2200/16; B01L 2300/021; B01L 2300/0816; B01L 2300/0825; B01L 3/545; G01N 33/94; G01N 35/1009; G01N 2001/007; G01N 35/00732; G01N 1/405; H04L 9/32; H04L 9/3278
See application file for complete search history.

(56) References Cited

U.S. PATENT DOCUMENTS

| | | |
|---|---|---|
| 2002/0199094 A1 | 12/2002 | Strand et al. |
| 2009/0057552 A1 | 3/2009 | Yamada et al. |
| 2011/0121165 A1 | 5/2011 | Watling et al. |
| 2015/0083797 A1* | 3/2015 | Tran ............. G09F 3/0298 235/487 |
| 2019/0013190 A1* | 1/2019 | Musselman ............ H01J 49/10 |

* cited by examiner

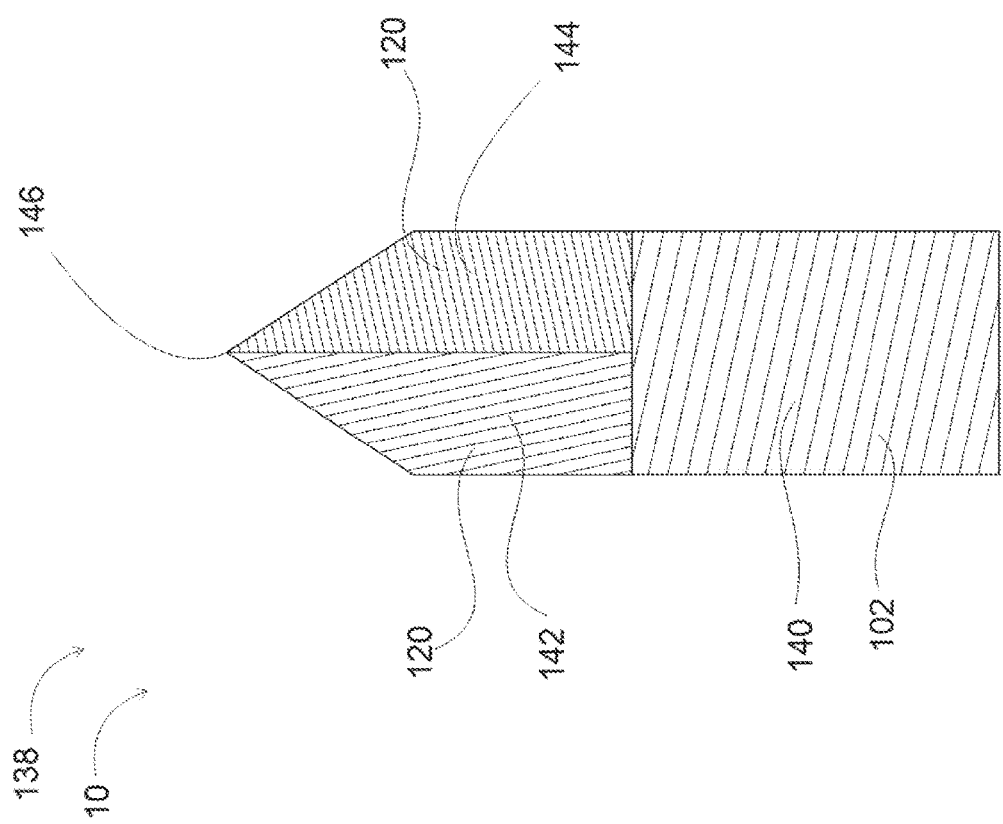

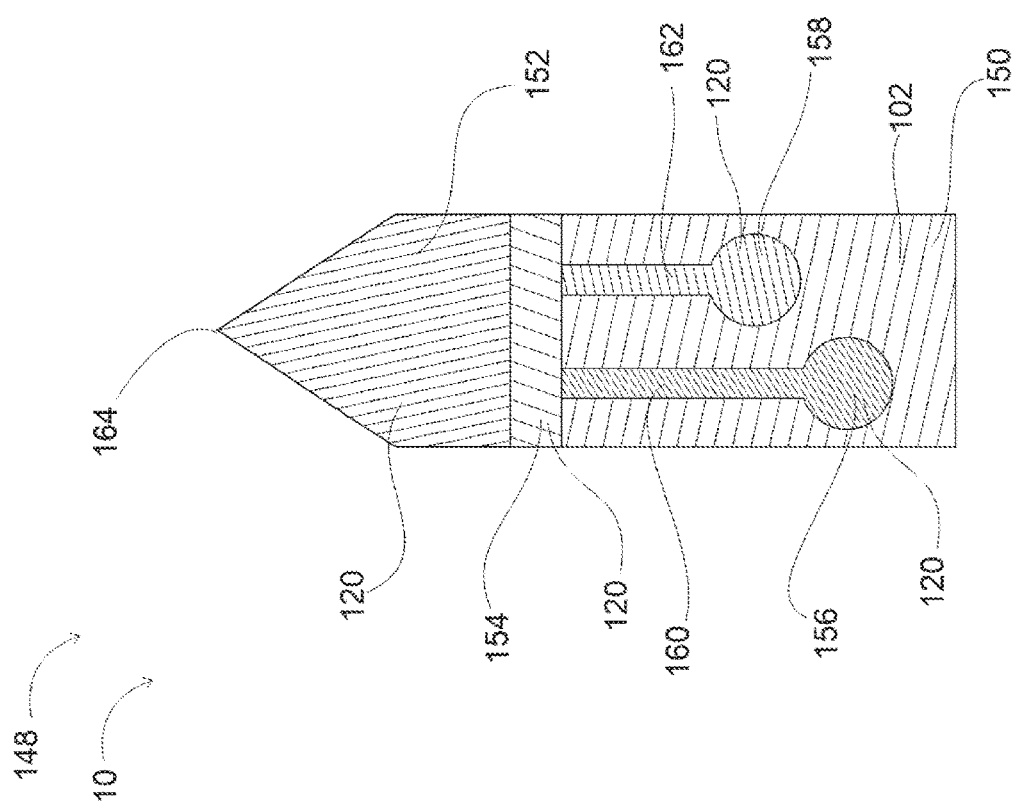

MOLECULAR CRYPTOGRAPHIC SAMPLING DEVICES AND METHODS OF MAKING AND USING

RELATED APPLICATIONS

This application claims the benefit of and priority to U.S. Prov. App. No. 62/874,763, filed Jul. 16, 2019, entitled "Unequivocal Identification of Samples and Sampling Devices via Molecular Cryptography on Smart Substrates and Methods Thereof," which is hereby incorporated by reference in its entirety.

FIELD OF THE INVENTION

This application is directed to devices for analytical chemistry that may be used for enrichment of molecules of interest present on or in complex matrices and methods for unique identification of such devices and the sample under scrutiny via molecular cryptography.

BACKGROUND OF THE INVENTION

Over the last 20 years, several technologies have been developed toward the direct interface of samples to mass spectrometry instrumentation for rapid qualitative and quantitative analysis. Among such technologies one can highlight direct analysis in real time (DART), desorption electrospray ionization (DESI), rapid evaporative ionization mass spectrometry (REIMS), liquid extraction surface analysis (LESA), mass spectrometer pen (Mass Spec-Pen), Desorption off Surface (DOS) probe, and the open probe sampling interface (OPSI). Although these developments facilitate sampling analytes of interest from the sample without any sample preparation, quantitation of analytes of interest at sub-part per billion (ppb) concentrations is limited. Besides, most of these technologies are constrained to the availability of said analytes in the surface of the sample under scrutiny.

Recently, attention has been placed on devices which collect and enrich analytes present on the sample under investigation. Modern literature has described devices which may be used to collect chemical information associated with the sample under study without having to collect the sample per se (i.e., microextraction of sample constituents). Although these technologies seem to be ideal for rapid analyte collection, analyte preservation, and analyte transfer toward the analytical instrumentation, none of them include a mechanism for characterizing whether the sample has been properly identified or it has been adulterated, exchanged, or destroyed.

BRIEF DESCRIPTION OF THE INVENTION

Herein we describe a sampling device which may be used to collect chemical information from a sample of interest and haul chemical information related to the identity of the sample and the sampling device. The device is composed of a solid substrate with one area, or multiple areas, which may be coated with one or diverse polymeric sorbents with the same or diverse physiochemical characteristics. Such device may be interfaced with mass spectrometry instrumentation using diverse platforms such as gas chromatography, liquid chromatography, ambient ionization, or any other sort of direct-to-MS technology. One or multiple areas of the device may be used to store chemical information, alien to the sample of interest, which is encrypted to the naked eye and uniquely correlated to the device and the sample of interest. Further, encrypted information may only be inferred with an algorithm which is linked unique identifying information, such as indicia engraved or embossed on the sampling device. In addition, some areas of said device may be used to store chemicals that can be used for calibration of the mass spectrometry instrumentation. Likewise, some areas of the device may be used to store deuterated analogues of the analytes of interest or internal standards which are used for quantitation of analytes of interest present in the sample under scrutiny. Similarly, in some areas of the device, a chemical reagent may be stored which may interact with either the analytes of interest or other molecular reagents stored in another section of the sampling device. In some aspects of the invention, the areas of the device where the sample is collected and the reagents are stored are discrete one from the other.

In one exemplary embodiment, a molecular cryptographic sampling device includes at least one unique identifying indicia disposed on the molecular cryptographic sampling device, a substrate including at least one depression disposed in or protrusion disposed on a surface of the substrate, at least one polymeric sorbent coating disposed on the at least one depression or protrusion, and at least one molecular encrypted code disposed on the at least one polymeric sorbent coating. The at least one molecular encrypted code includes at least one molecular tag, wherein the at least one molecular encrypted code is uniquely associated with the at least one unique identifying indicia in a database or by a predetermined algorithm.

BRIEF DESCRIPTION OF THE DRAWINGS

FIG. 1(d) is a front view of a molecular cryptographic sampling device having two different polymeric materials on the same side, according to an embodiment of the present disclosure.

FIG. 1(e) is a front view of a molecular cryptographic sampling device having two different polymer materials on the same side in different configurations, according to an embodiment of the present disclosure.

Wherever possible, the same reference numbers will be used throughout the drawings to represent the same parts.

DETAILED DESCRIPTION OF THE INVENTION

Figure 1A:
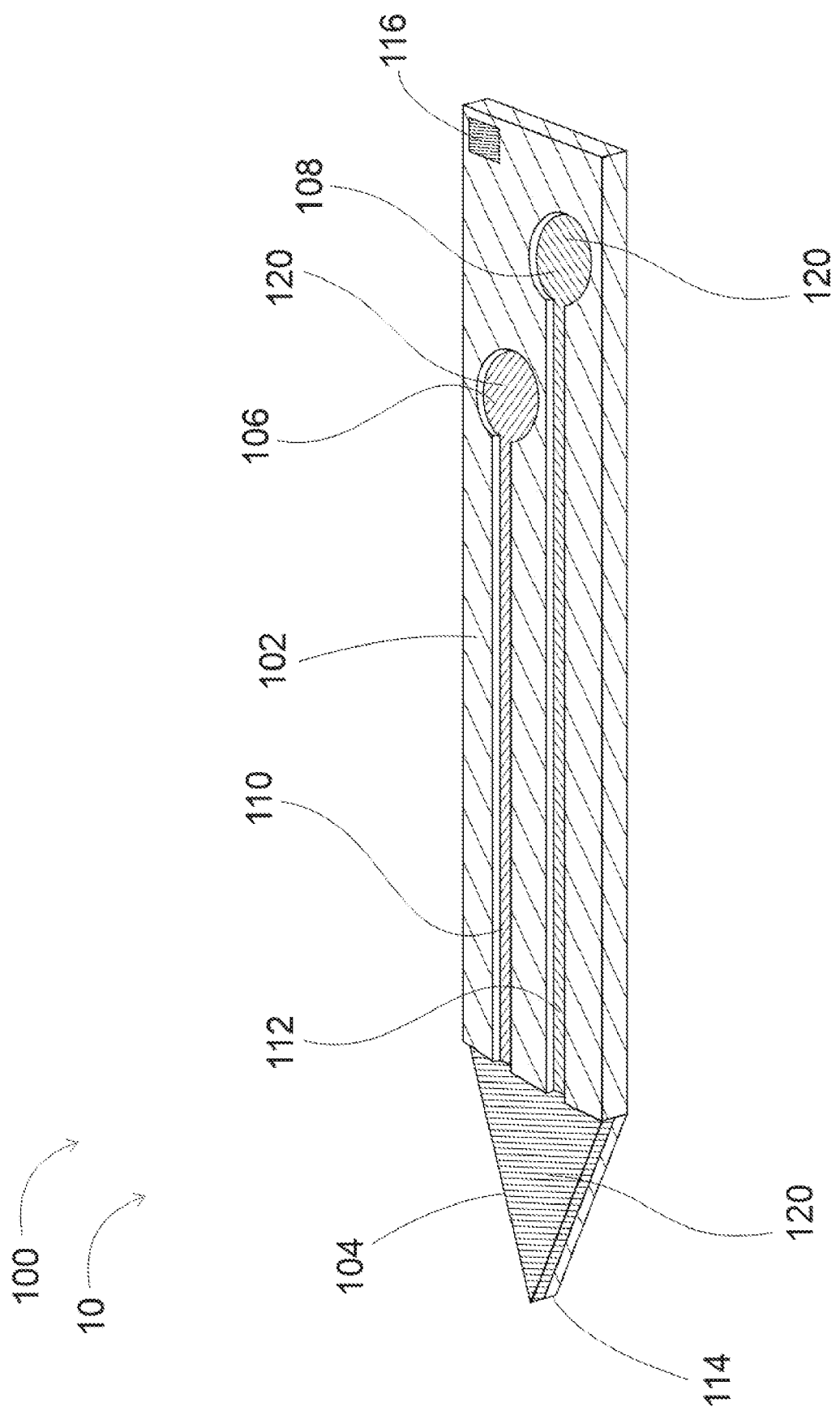
FIG. 1(a) is a perspective view, side view, a front view of a molecular cryptographic sampling device, according to an embodiment of the present disclosure.

The devices and methods herein described simultaneously isolate and enrich the analytes of interest present in a sample on a polymeric substrate. Thus, the devices herein described facilitate stabilization (quenching or collection) of compounds of interest, its transportation from the sampling place to the location where analysis is executed, and its direct transfer into the analytical instrumentation such as chromatographic equipment or directly into a mass spectrometer (MS). Moreover, said devices are pre-loaded with known concentrations/ratios of chemicals alien to the analytes of interest, hereinafter referred as molecular tags (MT), which are also correlated to a physical mark that is engraved or embossed on the sampling device. The chemical information stored on the sampling devices is unequivocally assigned to each sample/molecular cryptographic sampling device pair using an appropriate algorithm during the manufacturing process. Since the chemical information loaded on the sampling devices prior to the sampling is invisible to the bare eye, the chemical information may only be deciphered by running the samples on an analytical instrument and introducing the instrumental results to a deciphering algorithm provided by the manufacturer. The devices may be interfaced with diverse analytical instrumentation, such as MS, through liquid, laser or thermal desorption (e.g. via gas chromatography, liquid chromatography, or standalone mass spectrometry).

Furthermore, devices herein described may be utilized to calibrate mass spectrometers by preloading on at least one of the coated areas of the device a set of molecules that, when eluted/ionized, allow the MS system to adjust the accuracy of its mass to charge ratio measurements. In addition, MTs preloaded on the devices herein described may also be used to quantify target analytes collected on the sampling device. For instance, by using MT that comprise a series of isotopic analogues of the analytes of interest where said MT are pre-loaded in different amounts, this allows for internal calibration of said analytes of interest. Additionally, the devices may contain in one or more sections a series of reagents that react with either the analytes of interest or the molecular tags to generate derivatized analytes of interest or secondary molecular tags which are unique to the elution/ionization conditions and may only by deciphered by an algorithm provided by the manufacturer of said devices.

In many applications herein described, more than one device is employed for sampling from one or multiple samples, and the one or more sample may be arranged in a multi-vessel container which may be adjacent one another or in remote spatial and/or temporal locations. Further, there are many polymeric formulations available for analyte collection, but these formulations are difficult to distinguish with the naked eye. Moreover, one or more substrates with different substrate geometrical configurations may be used to scrutinize the same sample. Hence, it is conceivable that unintended or deliberated mixing up of the sampling devices is possible, in cases where multiple devices are employed, and, particularly, when the substrates are handled manually during the entire analytical workflow. Therefore, examples of applications where there is need for addressing of the sampling devices via chemical tagging include those listed below.

Identification of the substrate: in some aspects, there is precious little surface area on the substrate that is not occupied with polymeric sorbent. This creates a dilemma when considering where identification markings can be applied. Information such as substrate type, sorbent type, lot number, part number, etc. that is associated with new/unused molecular cryptographic sampling devices is then preferably marked directly onto the coated substrate by means of a chemical tag.

Identification of the use status of the substrate: in cases where multiple analyses are conducted, new substrates are indistinguishable from those that have been used from sampling. The invention here presented describes a device where information pertaining to the usage of the molecular cryptographic sampling device may be inferred from the data obtained after eluting/desorbing specific chemical tags unequivocally sorbed on the solid substrate.

Confirmation of the molecular cryptographic sampling device integrity and reliability of the data: in several examples, it is advantageous having a molecular tag that generates signal in the mass spectrometer that allows distinguishing between samples that test negative (i.e. no-analyte detected, but chemical tag detected) from those related to defective substrates, or defective instrumentation, that yield a false negative result (i.e. neither analyte nor chemical tag being detected).

Authenticity of the test: in several examples, it is advantageous having a molecular tag that generates a signal in the mass spectrometer that allows identifying the substrate at the time of analysis. In one case, the chemical information loaded in the device may be easily discerned during the analytical readout by the analyst (i.e., chemical information is provided to the analyst once the substrate is presented to the analytical instrumentation for analyte elution; single-blind experiment: sampling); while in another example the information is hidden or unavailable during the entire experimental workflow (i.e., chemical information loaded on the coated substrate is quite complex and cannot be easily discerned by the analyst during the analytical readout, such as chemical information loaded on the coated substrate being encrypted and only being decryptable using an algorithm provided by the manufacturer, providing a double-blind workflow where the analyst has no information regarding the authenticity of the test during sampling or analysis).

Chain of custody: in several examples, it is advantageous having knowledge of the substrate use status, particularly when it travels from the testing site (possibly remote from where the analysis is conducted) to the analysis location. As abovementioned, this is often important because of the size of the substrate (e.g., 0.050" substrate, roughly ⅛"×1" in size) and the ease of mixing them up (either accidentally or deliberately).

The present disclosure generally relates to systems and methods to collect, enrich and transport analytes of interest present on a sample (e.g. fluid, surface, semi-solid, gel, gas, or tissue) and, subsequently generate, via an analytical instrumentation such as a mass spectrometer, an instrumental response.

The molecular cryptographic sampling devices described herein include a solid substrate having either none, one, or multiple edges which may be used without further modification as an electrospray device for mass spectrometry analysis. Thus, the device is capable of performing analyte collection, analyte enrichment, analyte transportation, and analyte ionization.

The present disclosure also reports the interface of said device with diverse types of analytical instrumentation for measurement of the analytes collected wherein the analyte transfer to the instrument may be performed via liquid, thermal, or laser elution.

The devices and methods described herein may have one or more depressions or protrusions in one or more of the faces, and where each of those depressions or protrusions may be coated with a polymeric material, a polymer-metal oxide, or combinations of those materials. Wherein such coating materials may be used to either selectively remove undesired molecules, selectively enrich desired molecules, store molecular tags, or combinations of the foregoing. The depressions or protrusions may also contain a magnet or a magnetized material that collects either magnetic particles or magnetic molecules. Due to the well-defined geometry of the devices having one or more depressions or protrusions, elution of the analytes of interest may be performed with a high degree of spatial resolution.

In certain aspects, the present disclosure relates to systems and methods for direct ion generation using a molecular cryptographic sampling device having a substrate that considerably averts the contamination and/or damage of the mass spectrometer inlet because the device extracts the target analytes while avoiding other sample components such as salts, proteins, carbohydrates, and detergents.

In some specific embodiments, the present disclosure relates to systems and methods for direct ion generation using a substrate that facilitates the extraction of large molecules such as peptides and proteins. In some preferred examples, the polymeric material facilitates the adsorption/ elution of molecules with a molecular weight larger than 1,000 Daltons. In some particular examples, the sample is spotted onto the coated substrate and allow to dry for analysis. Primarily, large molecules are capture on the surface of the sorbent.

In some aspects, the molecular cryptographic sampling device substrate has a portion coated with an extraction polymer. The substrate is preferably flat and with a curved or elliptical end and may interface with chromatographic systems or stand-alone mass spectrometers. In some preferred examples, the molecular cryptographic sampling device may have a pointed end that may be used to generate an electrospray.

The substrate may be any suitable material, including, but not limited to, a metal, a metal alloy, a glass, a fabric, a polymer, a polymer metal oxide, or combinations thereof. The substrate may include, by way of non-limiting example, nickel, nitinol, titanium, aluminum, brass, copper, stainless steel, bronze, iron, or combinations thereof. Similarly, the substrate may include any material used for additive manufacturing, 3D printing, lithography, or circuit manufacturing, such as, but not limited to, silicon wafer, glass fiber reinforced polymer (fiberglass), polytetrafluoroethylene, polyimide film, polycarbonate-acrylonitrile butadiene styrene (PC-ABS), polybutylene terephthalate (PBT), polylactic acid, poly(methyl methacrylate), polycarbonate (PC), acrylonitrile butadiene styrene (ABS), polyetherimide (e.g., ULTEM™), polyphenylsulfone (PPSF), polycarbonate-ISO (PC—ISO), or combinations thereof.

Mass spectrometry systems that include molecular cryptographic sampling devices are also described. Methods of analyzing a molecule previously collected from a sample either onto the polymeric sorbent on the molecular cryptographic sampling device, or the bare magnetic particles captured on the substrate, or the coated magnetic particles captured on the substrate, or the functionalized magnetic particles captured on the substrate are also herein described.

Methods for encrypting and deciphering molecular information stored on the molecular cryptographic sampling devices are herein presented. In some examples, molecular encryption may be stored in the entire coated area of the substrate. In other examples, molecular encryption is selectively deposited on defined areas of the substrate of the molecular cryptographic sampling device. Methods and devices for deciphering molecular encryption stored within a defined spatial location on the substrate are also herein described. Likewise, methods and devices used for delivering or depositing the molecular tags on the substrate are also herein described.

Mass spectrometry systems that include the molecular cryptographic sampling device and further enhancements to the coated blade spray interface described by U.S. Pat. No. 9,733,234 are also herein described. Particularly, herein it is described the orthogonal spray of molecular cryptographic sampling devices onto mass spectrometry instrumentation via substrate spray ionization. Methods for enhancing instrumental response and spray stability over the time, when compared to horizontal electrospray ionization (ESI) via traditional coated blade spray, are also described.

Methods for calibration of the mass spectrometer system or an ion mobility system, while performing an instrumental sequence with molecular cryptographic sampling devices are also described. Methods that allow for derivatization of the target analytes in liquid phase are also described. Methods that allow for efficient cleaning of the inlet of the mass spectrometer after any experiment with a molecular cryptographic sampling device are also described.

Methods for the automated interface of multiple molecular cryptographic sampling devices are also herein described.

The transitional term "comprising" is synonymous with "including," or "containing," and is inclusive or open-ended and does not exclude additional, unrecited elements or method steps.

The transitional phrase "consisting of" excludes any element, step, or component not specified in the claim, but does not exclude additional components or steps that are unrelated to the invention such as impurities ordinarily associated with a composition.

The transitional phrase "consisting essentially of" limits the scope of a claim to the specified materials or steps and those that do not materially affect the basic and novel characteristics of the claimed invention.

As used herein, unless indicated to the contrary, "about" indicates a value tolerance of ±10% of the value being modified by "about."

In some examples, a substrate of a molecular cryptographic sampling device may comprise a "solid phase microextraction" (SPME) device. In other examples, a molecular cryptographic sampling device may be a coated blade spray, an enhanced coated blade spray, or a magnetic blade spray.

The expression "analyte of interest," "target analyte" (TA) and "compound of interest" should be understood to be synonymous. In some examples, a compound of interest may be a "chemical of interest" or a "molecule of interest."

The expression "molecular tag" (MT) is a broad term encompassing" ID tags" (IDT), "molecular internal standards" (MIS), and "molecular reactive tags" (MRT). In some examples, a molecule used to encrypt the information may also be referred to as a "chemical tag," "internal standard," "internal calibrant," or "internal reactive reagent." Said molecular tags are used in combination with an algorithm to cypher information related to the device under scrutiny and it is unique to the identity of every substrate 100 of each molecular cryptographic sampling device 10.

The expressions "analyte collection," "analyte extraction," "analyte enrichment," and "analyte loading" are intended to be understood as synonymous terms form a practical perspective as these refer to the act of taking molecules from one location to another (e.g., from the sample under scrutiny to the instrument when there measurement of the target analyte is performed).

The terms "extractive material," "sorbent," "adsorbent," "absorbent," "polymeric phase," "polymer sorbent," "magnetic particles," "coated magnetic particles," and "functionalized magnetic particles" are intended to be synonyms from a practical perspective as these refer to the material use to collect the analytes of interest, molecular tags, and any combinations thereof.

The expressions "loading," "depositing," "printing," "delivering," "spraying," "dispensing," and "pipetting" are intended as being synonyms when referring to the deposition of fix amounts of molecular tags on the substrate.

In one embodiment, a molecular cryptographic sampling device 10 includes at least one unique identifying indicia 116 disposed on the molecular cryptographic sampling device 10, a substrate 102 including at least one depression 104, 106, 108 disposed in or protrusion 122, 124, 126 disposed on a surface of the substrate 114, at least one polymeric sorbent coating 120 disposed on the at least one depression 104, 106, 108 or protrusion 122, 124, 126, and at least one molecular encrypted code disposed on the at least one polymeric sorbent coating 120, the at least one molecular encrypted code including at least one molecular tag, wherein the at least one molecular encrypted code is uniquely associated with the at least one unique identifying indicia in a database or by a predetermined algorithm.

The systems and methods disclosed herein termed as molecular cryptographic sampling devices 10 have either none, one, or multiple depressions 104, 106, 108. The expression "depression" should be understood as being synonymous with "well," "dent," and "indentation." The depressions 104, 106, 108 may be coated with an extractive phase that comprises a polymer, polymeric particles or combinations thereof. The extractive phase 120 used to enrich and collect the analytes of interest may include solid phase microextraction (SPME) particles, solid phase extraction (SPE) particles, bare magnetic particles, polymeric coated magnetic particles, functionalized magnetic particles, or combinations thereof. The extractive phase 120 may comprise a biocompatible polymer or extraction particles bound to the substrate surface using a biocompatible binder. The depression in the substrate 102 may include a magnetized portion which may capture coated magnetic particles, bare magnetic particles, magnetic molecules, or combinations thereof. Yet, a person of skill in the art would understand that the substrate 102 might be fully magnetic allowing for capturing coated magnetic particles, bare magnetic particles, magnetic molecules, or combinations thereof.

In some embodiments, the surface of the substrate 102 is non-homogenously coated with one or more polymeric sorbents 120. In preferred examples, the surface of the substrate 102 has well-defined protrusions made of the extractive material. The expression "protrusion," "protuberance," and "lump" should be understood to be synonymous. A person of skill in the art would understand that these protrusions 122, 124, 126 may be made using different coating procedures including, but not limited to, sputtering, spraying, or screen-printing. In some embodiments the thickness of the protuberances is 100 μm. In particularly preferred examples, the thickness is less than 20 μm. In some examples, the protrusions are discrete one from another and connected by well-defined channels 128(a) and 128(b). Such channels may be either protuberances or depressions on the substrate 102. Channels 128(a) and 128(b) may be protrusions or depressions on the substrate 102. The channels 128(a) and 128(b) are preferable protrusions if the polymeric sorbent coating 120 is applied to the substrate 102 as a protrusion or indentations if the polymeric sorbent coating 120 is applied to the surface of the substrate 102 as an indentation. Channels may be coated with the same or different polymeric sorbent coating 120 than the protuberance(s). Channels may be coated with the same or different polymeric sorbent coating 120 than the indentation(s) Channels may be preferably coated with same polymeric sorbent coating 120 as in the protuberances or the indentations.

In some preferred examples, the molecular cryptographic sampling device 10 herein described has a length from about 1 cm to about 10 cm; a width from about 0.1 mm to about 5 mm; and a thickness from about 100 μm to about 2 mm. In certain examples, the length is about 4 cm to about 5 cm, alternatively about 4.5 cm, the width is about 2 mm to about 4 mm, alternatively about 3 mm, and/or the thickness is about 0.1 mm to about 0.5 mm, alternatively about 0.3 mm.

Figure 1B:
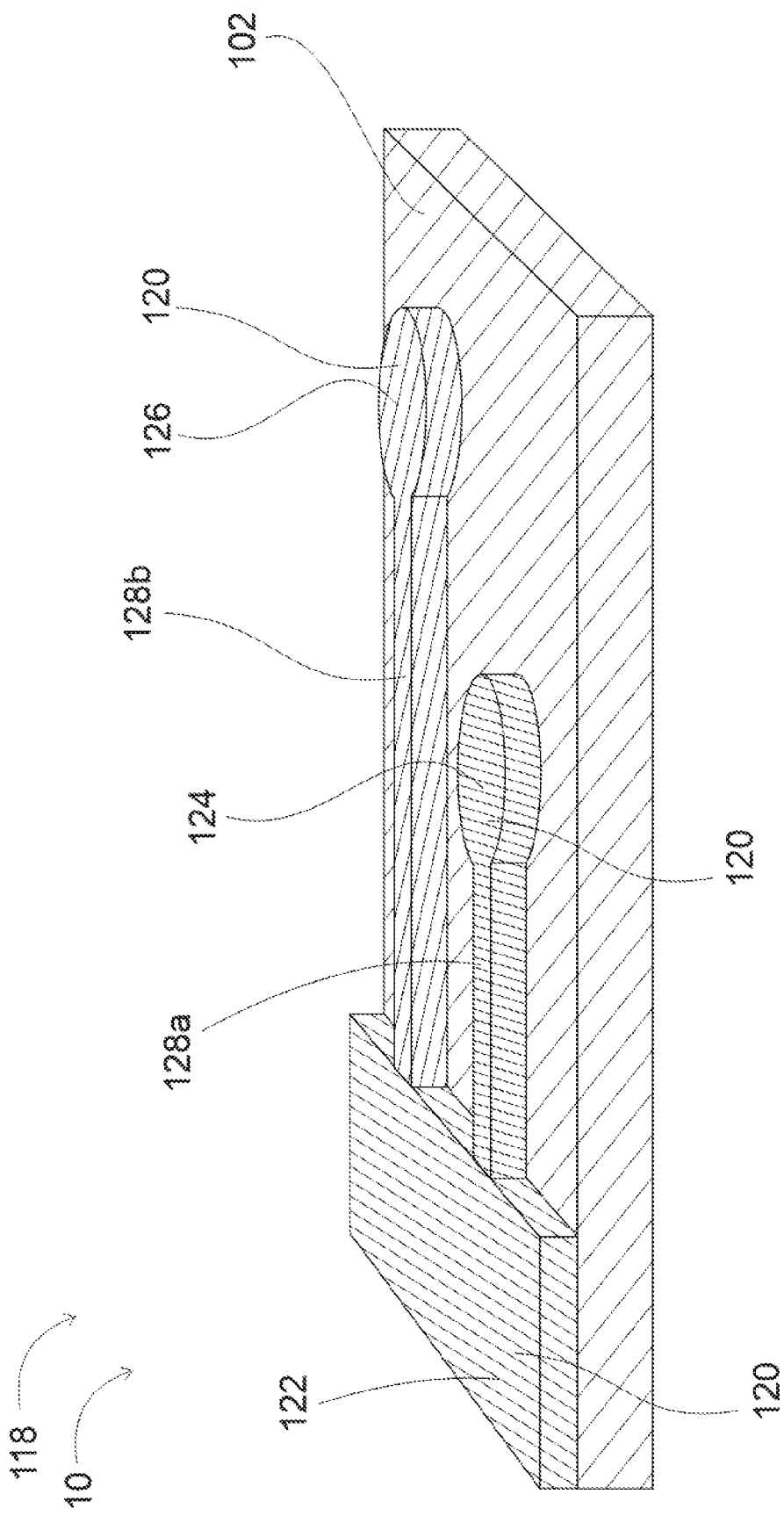
FIG. 1(b) is a perspective view of a molecular cryptographic sampling device having a rectangular shape, according to an embodiment of the present disclosure.

In some embodiments, the substrate 102 lacks a pointed tip and comprises a flat sheet with either a squared, curved, or elliptical end as shown in FIG. 1(b). In another example, the substrate 102 may have a pointed end 114 and it may have an angle from 8° to 180°, alternatively an angle from 20° to 60° as shown in FIG. 1(a). The substrate 102 may be coated with enough extraction polymer to result in a coated area of at least 0.01 mm². In various examples, the coated area is from about 0.1 mm² to about 100 mm², alternatively about 10 mm².

FIG. 1(a) illustrates one embodiment of a molecular cryptographic sampling device 10 with a pointed tip 114 which may be used to generate ions via electrospray ionization. The molecular cryptographic sampling device 10 comprises a substrate 102 with one pointed end 114 and one or multiple chemical loading zones (e.g., 104, 106, 108) and in some embodiments, said chemical loading zones are discrete from one another and connected by well-defined channels 128(a) and 128(b).

FIG. 1(b) illustrates one embodiment of a molecular cryptographic sampling device 10 with a square tip 122. The loading zones (e.g., 122, 124, 126) with depressions/protrusions, may be coated with the same or different extractive materials. Some of the loading zones, or depressions/protrusions, comprise a coating material 122 that enriches molecules of interest. Since the coating 104 may be adjusted for analytes of interest, devices and methods disclosed herein may reduce undesirable artefacts that might lead to ionization suppression, ionization enhancement, molecule transformation, instrument contamination, or combinations thereof.

Figure 1C:
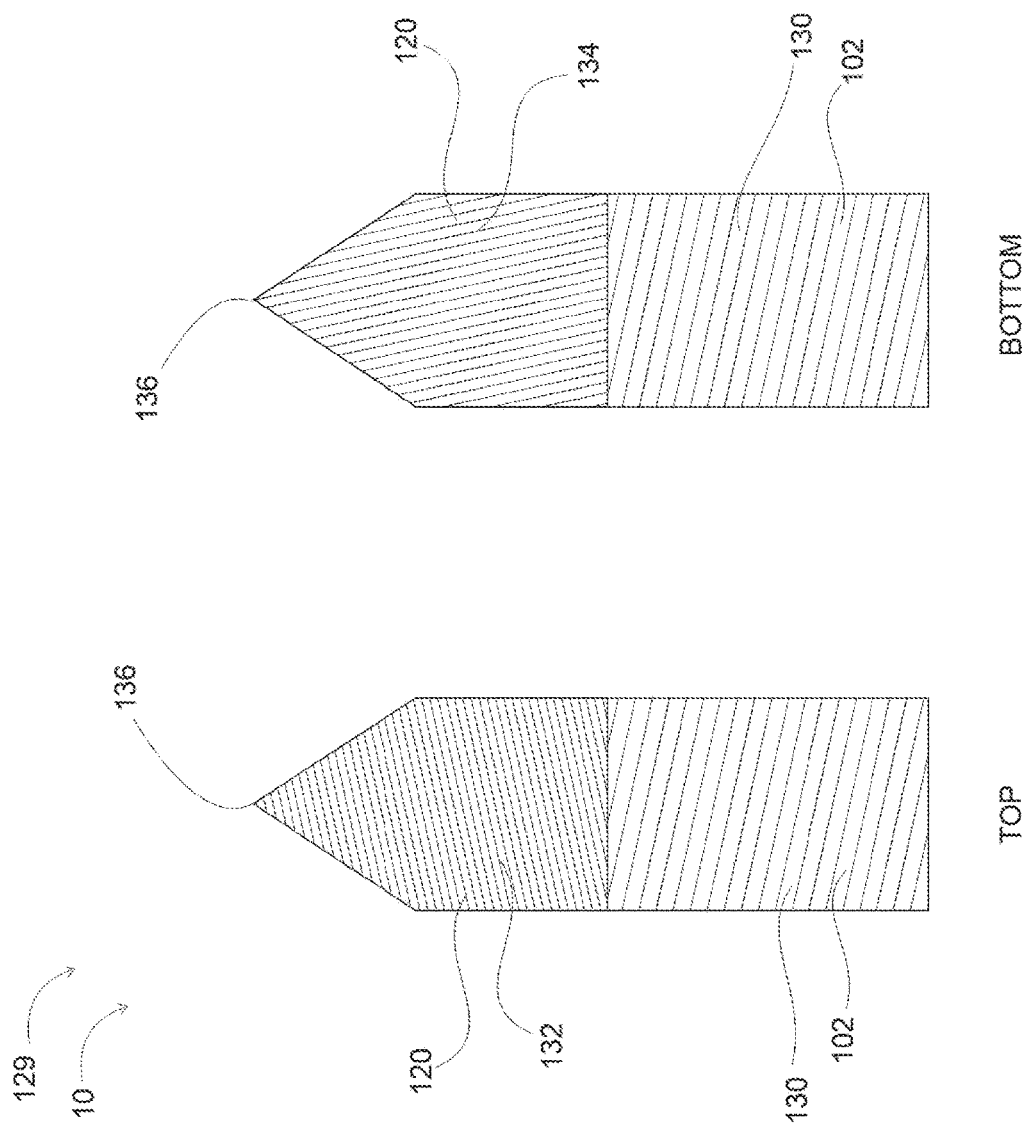
FIG. 1(c) is a front and back view of a molecular cryptographic sampling device having two different polymeric materials on different sides, according to an embodiment of the present disclosure.

In some examples, each side of the molecular cryptographic sampling device 10, 128 is coated with two different types of polymeric material 132 and 134 on the analyte loading zones as shown in FIG. 1(c). A person of skill in the art would understand that coatings on each side of the substrate 100 may also be made using different coating procedures including, but not limited to, spraying, sputtering, screen-printing, or combinations thereof. In some preferred examples, one side of the substrate 100 is coated with two or more different types of polymeric sorbent as shown in FIG. 1(d). Multiple polymeric adsorbents may be deposited on the substrate 100 using coating procedures such as screen-printing. The polymeric materials deposited on either side of the molecular cryptographic sampling device 10 may be coated to the nearest proximity of the tip 136, and when used, a voltage may be applied to the non-coated area 130.

In some preferred examples of the molecular cryptographic sampling device 10, 138, the substrate 102, 140 is covered with two different polymeric adsorbents 142 and 144 symmetrically arranged on one side of the surface as shown in FIG. 1(d). In particular experiments elution of the analytes from loading zones 142 and 144 may be performed with temporal and spatial resolution. In other embodiments, the elution TA and MT from loading zones 142 and 144 can be performed simultaneously to provide a broad range of analyte coverage (i.g., polar and non-polar compounds). In either case, the two different polymeric materials are deposited to the nearest proximity of the tip 146.

In other examples of the molecular cryptographic sampling device 10, 148, the substrate 102, 150 is covered with a stack of multiple and diverse polymeric adsorbents adjacent one to another as shown in FIG. 1(e). The molecular cryptographic sampling device 10 may include different loading zones 152, 154, 156, and 158 which may be coated with the same or with different polymeric materials that are interconnected one to another via well-defined channels 160, 162. In some particular examples, the loading zone 152, which is proximal to the tip 164, comprises a polymeric sorbent that facilitates the removal of undesired matrix components such as pigments or phospholipids.

Figure 1F:
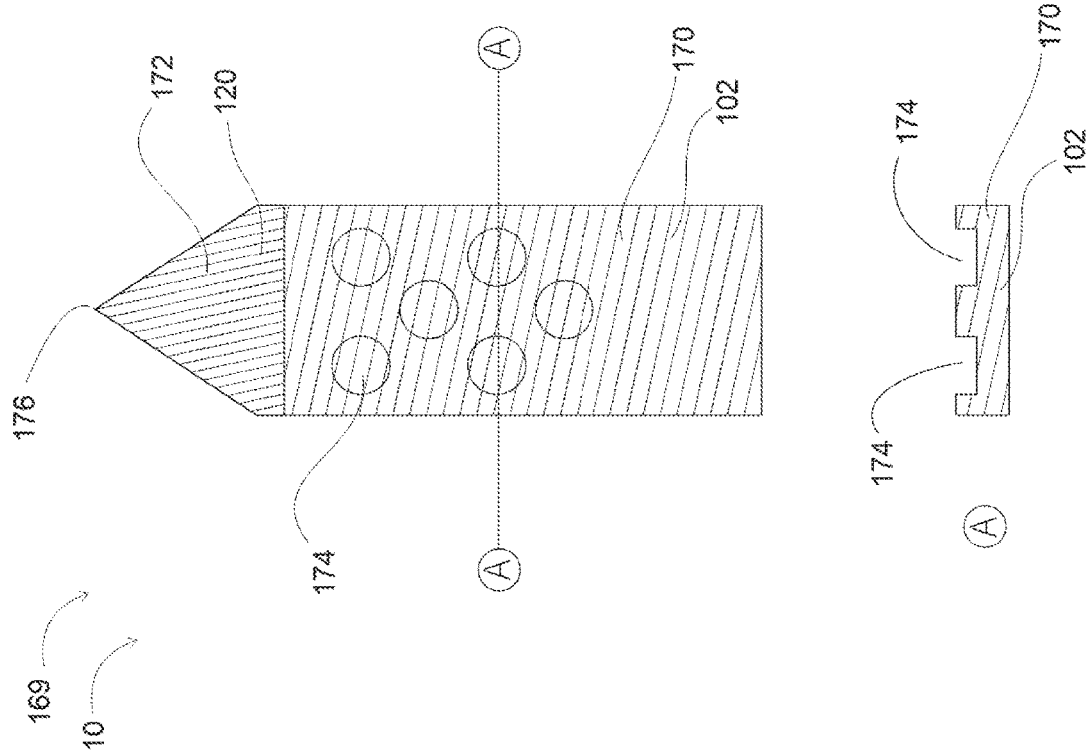
FIG. 1(f) is a front and side view of a molecular cryptographic sampling device having surface holes, according to an embodiment of the present disclosure.

In some particular embodiments of the molecular cryptographic sampling device 10, 169 (as shown in FIG. 1(f)), a non-coated surface 170 has specific patterns on the surface, such as holes 174 that facilitate the accumulation of elution solvent and controlled release of the elution solvent onto to the loading zone 172 which is in proximity with the tip 176. This feature is useful when the molecular cryptographic sampling device 10 is used for electrospray orthogonally to a MS. The holes 174 are located at the back of the coated area 172.

Figure 1G:
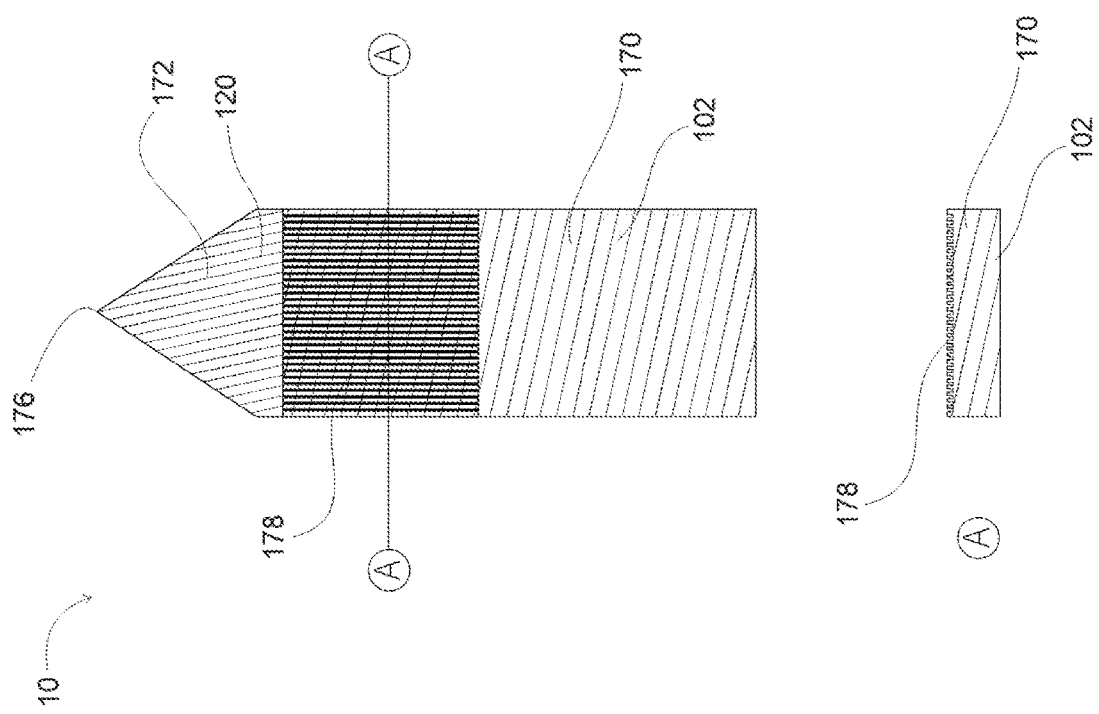
FIG. 1(g) is a front and side view of a molecular cryptographic sampling device having surface grooves, according to an embodiment of the present disclosure.

In some particular embodiments of the molecular cryptographic sampling device 10 (as shown in FIG. 1(g)), a non-coated surface 170 has specific patterns on the surface, such as grooves 178 that facilitate the accumulation of elution solvent and controlled release of the elution solvent onto to the loading zone 172 which is in proximity with the tip 176. This feature is useful when the molecular cryptographic sampling device 10 is used for electrospray orthogonally to a MS inlet instead of horizontally. The holes 178 are located at the back of the coated area 172.

Figure 1H:
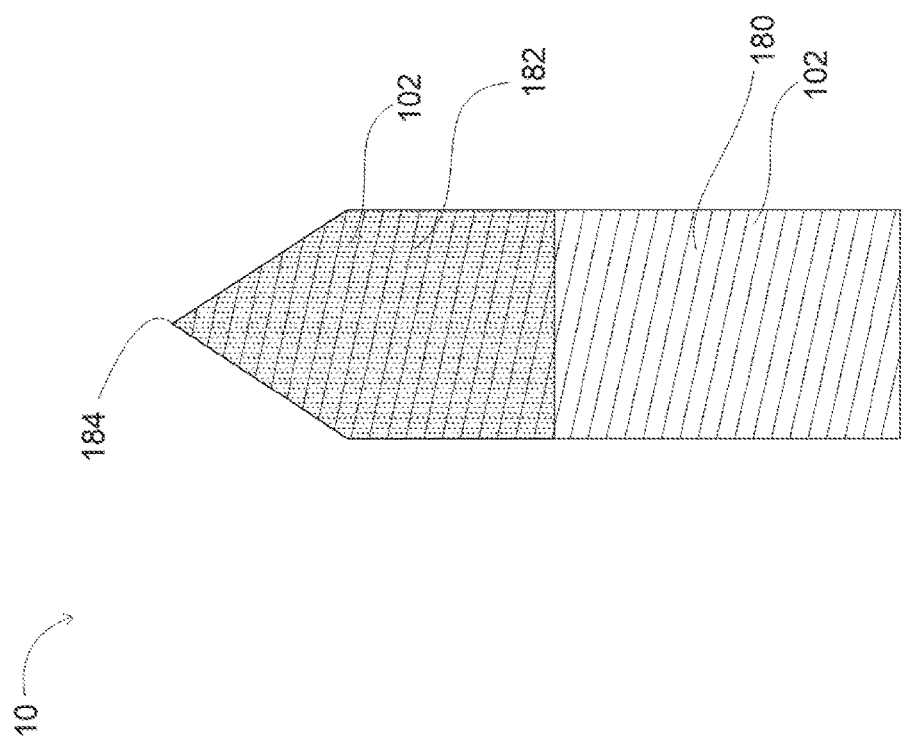
FIG. 1(h) is a front view of a molecular cryptographic sampling device having a rough surface for increased matrix adhesion, according to an embodiment of the present disclosure.

In some specific examples of the molecular cryptographic sampling device 10 (as shown in FIG. 1(h)), the molecular cryptographic sampling device 10 is not used to collect small molecules on the loading zones. Rather, the molecular cryptographic sampling device 10 is used to collect and transport the entire matrix. Hence, after immersing the molecular cryptographic sampling device 10 in the matrix, this is allowed to dry. Alternatively, a droplet of the matrix can be deposited as a spot on the surface of the substrate 180 and allowed to dry. In this particular example, the coating 182 on the substrate 180 has a rough surface providing better adhesion of the matrix on the substrate 180. The tip 184, located in proximity to the coating 182, may be used to generate an ESI signal of the sample under scrutiny. Unlike other devices herein described, this embodiment is not intended to provide an extensive sample clean-up, but rather to provide simple transportation of the sample of interest and stable ESI generation via tip 184.

In some examples, some of the loading zones 106, 108 as shown in FIG. 1(a) may also be used to store other molecules, such as molecular tags (MT) that are alien to the sample under scrutiny but uniquely correlated to the sampling device and the sample under study.

Essentially, an MT is a molecule, organic or metal-organic, external to the sample to be scrutinized that is stored in one or more of the loading zones of the solid substrate. Further, the MT should ionize under the same mechanism of the TA, but it should not interfere with the screening, detection, and/or quantitation of the TA(s).

An ID tag (IDT) is a type of MT which may also be used to unequivocally identify both the sample under scrutiny and the molecular cryptographic sampling device. It should be understood that the IDT must ionize under the same mechanism of the TA, but it should not interfere with the screening, detection, and/or quantitation of the TA(s).

A molecular calibrant (MC) is a type of MT that is used to calibrate the instrumentation used to measure the IDT and TA. Likewise, the MC should ionize under the same mechanism of the TA, but it should not interfere with the screening, detection, and/or quantitation of the TA(s) or the IDT(s). MC are used to correct for drifts and/or changes in the instrumental response because of changes in the humidity, temperature among other factors.

A molecular Internal Standard (MIS) is a type of MT that resembles the TA, yet, with different mass to charge (m/z) values. One useful example of an MIS would be essentially isotopic labelled analogue(s) of the TA. Multiple MIS can be stored on one or multiple loading zones 106 and used, not only to correct for potential signal drifts, but also to quantify the TA. Hence, under controlled analyte collection conditions from a known/normalized sample, it is possible knowing what the extraction rate of the coating material is for said analyte and, as a result, it is possible to calibrate for said analyte using the MIS. Hence, under fixed extraction conditions (e.g., sample temperature, sample volume, sample agitation speed), it is possible to determine the amount of the MIS that needs to be deposited on the loading zone(s) 106 or 108, prior to extraction of the TA.

A molecular encrypted code (MEC) is a group of molecular tags which have been deposited in one of the loading zones at a fixed amount each. Therefore, when said MTs are eluted from the loading zone and injected onto the instrument used for analysis, these generate an instrumental signal which is unique to the substrate and the sample under scrutiny. In cases where the molecular cryptographic sampling device 10 is directly interface with an analytical instrument, such as a mass spectrometer, a unique set of ion ratios read outs are generate which unequivocally correspond to that molecular cryptographic sampling device 10. The amount of each MT to be deposited on the loading zones is determine by a computer algorithm. Likewise, the algorithm determines the number and the class of MTs to be deposited on the loading zones depending on the application. An MEC may be comprised the combination of at least two of the following MTs: IDT(s), and/or MC(s), and/or MIS(s). The factors use for encryption include, but are not limited to, the number of molecular tags, the class of the molecular tag and the amount of each molecular tag on the loading zone. The MEC is unique to every substrate/sample pair and it is related to an indicial 16 disposed on the substrate.

A molecular reactive reagent (MRR) is a molecule, organic or metal-organic, alien to the sample to be scrutinized that can be placed on the elution/ionization fluid (e.g. an elution solvent for liquid chromatography or substrate spray ionization). The MRR may react either with the TA and/or with other IDTs. Alternatively, the MRR may also be deposited in one of the loading zones of the molecular cryptographic sampling device 10 and eluted using either thermal, liquid, or laser desorption.

A molecular reactive tag (MRT) is a type of MT that can react either with a TA, and IDT or a molecular reactive reagent (MRR) to generate a molecularly encoded product (MEP). Hence, when reacting with the TA, the MEP not only is unique to the sample and the molecular cryptographic sampling device 10, but may only be generated when the TA is present in the sample under scrutiny. Therefore, MEP generated from a TA may lead not only to better sensitivity (particularly for molecules with poor ionization efficiencies or high instrumental noise) but also to enhance selectivity and unequivocal sample identification. When reacting with an IDT, the MEP may be used to determine whether the molecular cryptographic sampling device 10 has been used or not. In such an example, the MEP becomes a new IDT and part of the MEC. Likewise, when the MRT reacts with an MRR it may also be used to determine whether the molecular cryptographic sampling device 10 has been used or not. Unlike the former case, the reaction of an IDT with an MRR does not require a substrate with a spatially resolved distribution. Whereas in the case of IDT interacting with an MRT to generate an MEP, the substrate 102 must have a well-defined geometry, where the MT are stored at different spatial locations such as 106 and 108. In such configurations, time course of the reaction may be controlled by the analyst and the instrumentation used for analysis/elution of the TA and the MTs from the molecular cryptographic sampling device 10.

Figure 2:
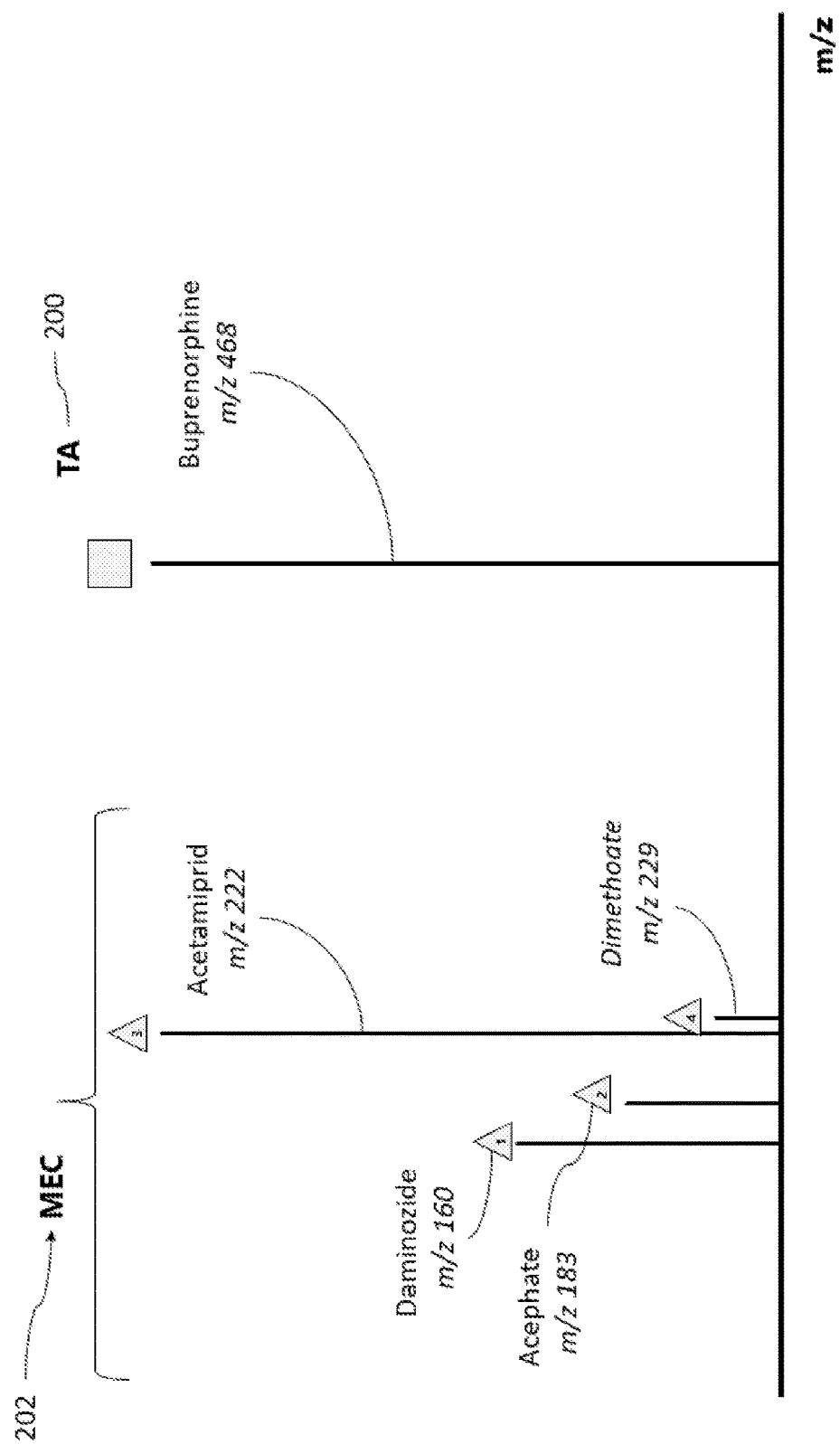
FIG. 2 illustrates the mass spectra of buprenorphine (m/z 468) as the target analyte, extracted from human urine samples, when using acetamiprid (m/z 222), acephate (m/z 183), daminozide (m/z 160) and dimethoate (m/z 229) as the molecular encrypted code, according to an embodiment of the present disclosure.

Examples of IDT include isotopic labeled analogues of the TA, as well as any other molecule foreign to the TA under study. For instance, FIG. 2 illustrates the mass spectra of buprenorphine (m/z 468), as the TA 200 extracted from human urine samples when using acetamiprid (m/z 222), acephate (m/z 183), daminozide (m/z 160), and dimethoate (m/z 229) as the IDT comprising the MEC 202. The amount(s) and, consequently, ion ratio(s) of each of the four MTs is unique to the molecular cryptographic sampling device 10 used to collect buprenorphine from the urine sample presented in FIG. 2. Semi-quantitative determination of each of the IDTs may be performed by measuring the instrumental response as a function of the area under the curve after the mass spectrometry experiment is completed.

Figure 3:
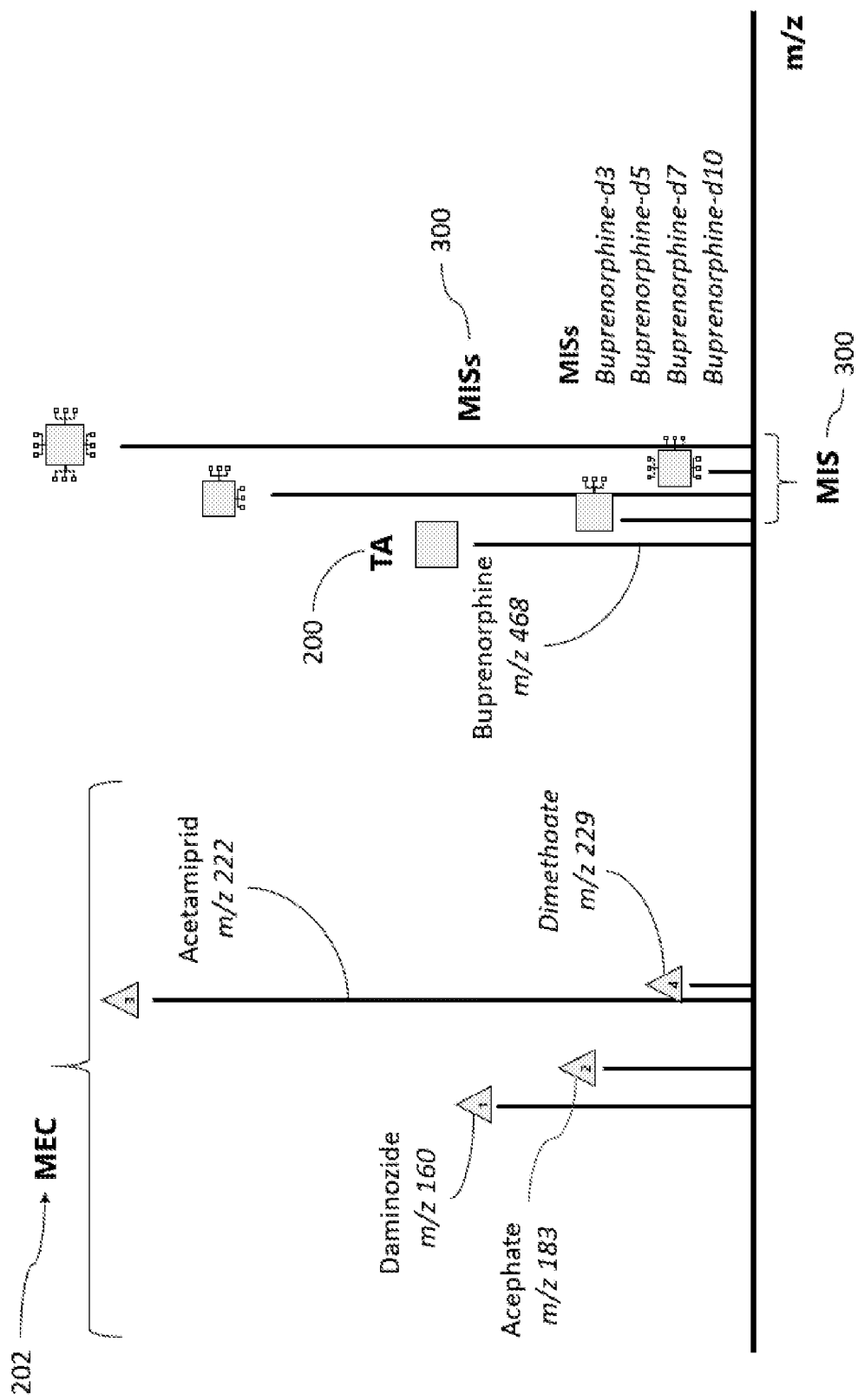
FIG. 3 illustrates the mass spectra of buprenorphine (m/z 468) as the target analyte, extracted from human urine samples, when using acetamiprid (m/z 222), acephate (m/z 183), daminozide (m/z 160) and dimethoate (m/z 229) as the set of ID tags comprising the molecular encrypted code and buprenorphine-d3, buprenorphine-d5, buprenorphine-d7 and buprenorphine-d10 as the set of molecular internal standards, according to an embodiment of the present disclosure.

FIG. 3 illustrates the mass spectra of buprenorphine (m/z 468) as the TA 200 extracted from human urine samples when using acetamiprid (m/z 222), acephate (m/z 183), daminozide (m/z 160), and dimethoate (m/z 229) as the set of IDT comprising the MEC 202, and buprenorphine-d3, buprenorphine-d5, buprenorphine-d7 and buprenorphine-d10 as the set of MIS 300. As previously stated, a set of MIS spiked at different amounts on the loading zone may be used to calibrate the amount of TA collected on the molecular cryptographic sampling device 10 under controlled collection conditions. The amount of buprenorphine in the sample may be back-calculated using a calibration curve constructed based on the instrumental response attained for each MIS (or deuterated analogue) against the concentration of the MIS (i.e., amount of each MIS loaded on the sorbent material; said amount is deposited on the loading zone based on known collection rates at fixed TA extraction conditions).

Figure 4:
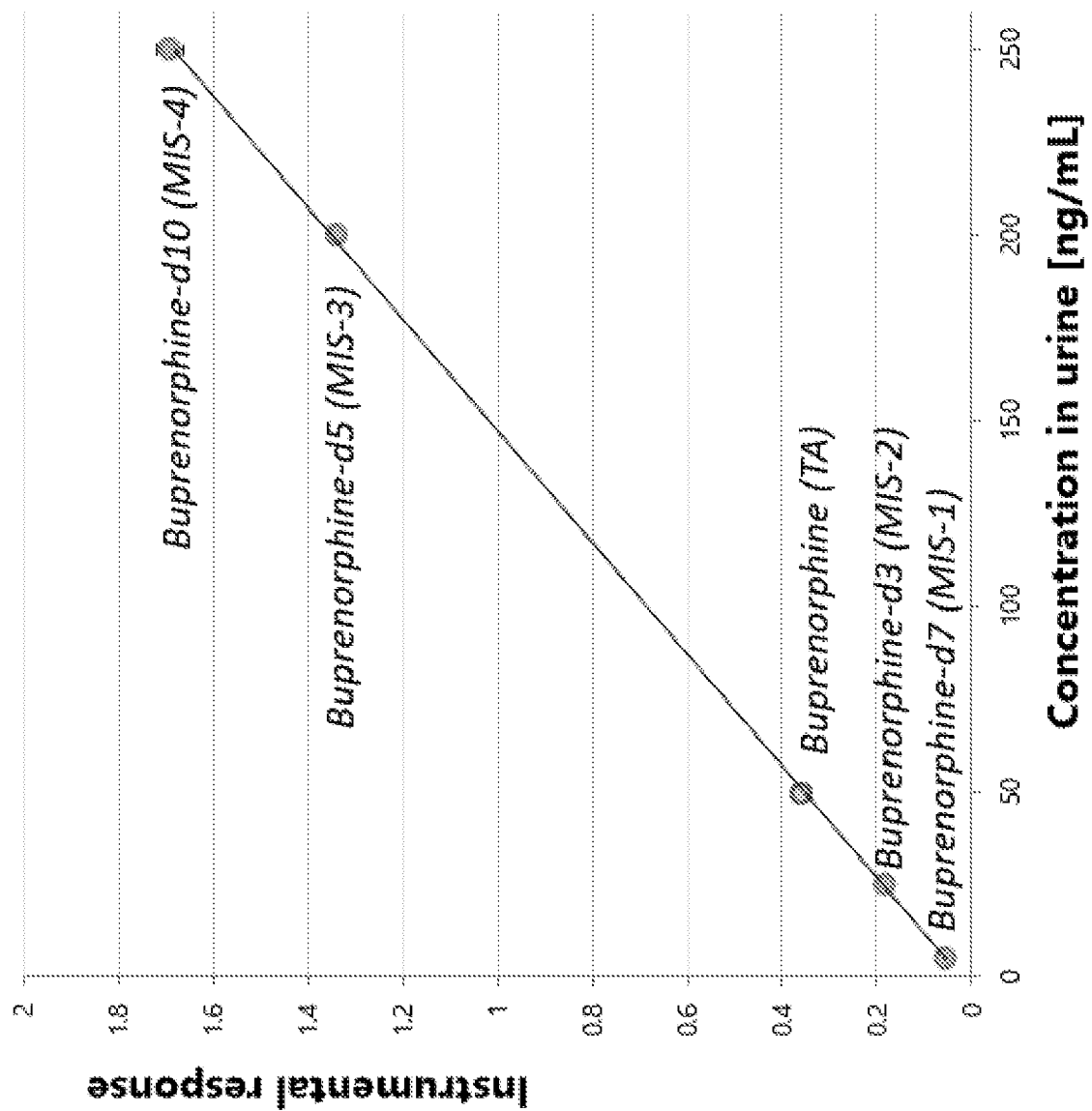
FIG. 4 illustrates a calibration curve for buprenorphine in urine samples when using molecular internal standards pre-loaded in one of the loading zones of the molecular cryptographic sampling device, according to an embodiment of the present disclosure.

FIG. 4 illustrates a calibration curve for buprenorphine in urine samples when using diverse MISs 300 pre-loaded in one of the loading zones 106 of the molecular cryptographic sampling device 10. Analyte collection (buprenorphine) was performed in the loading zone 104 coated with HLB particles. Extractions were performed from urine samples spiked with at 50 ng/mL. The amount of MISs 300 to be pre-loaded on the loading zone 106 was determined based on the extraction rate of the coating at fixed extraction conditions (e.g. sample volume, sample temperature, sample agitation rate). The MISs, labelled as MIS-1 (buprenorphine-d7), MIS-2 (buprenorphine-d3), MIS-3 (buprenorphine-d5), and MIS-4 (buprenorphine-d10) were preloaded at known amounts based on the extraction rate of buprenorphine on the molecular cryptographic sampling device 10 under the fixed extraction conditions. Quantitation of the TA (buprenorphine) was performed by using the linear regression attained for the area under the curve of each of the MIS when collecting data via a tandem mass spectrometry (MS/MS) experiment. When using the MISs 300 as calibrators for quantitation of the TA 200, it is possible to conduct the sampling, sample preparation and sample quantitation with a single molecular cryptographic sampling device 10. In addition, when preloading MEC 202 on the same loading zone 106, or independent loading zone 108, it is possible to execute both analyte quantitation and sample/device identification.

Figure 5:
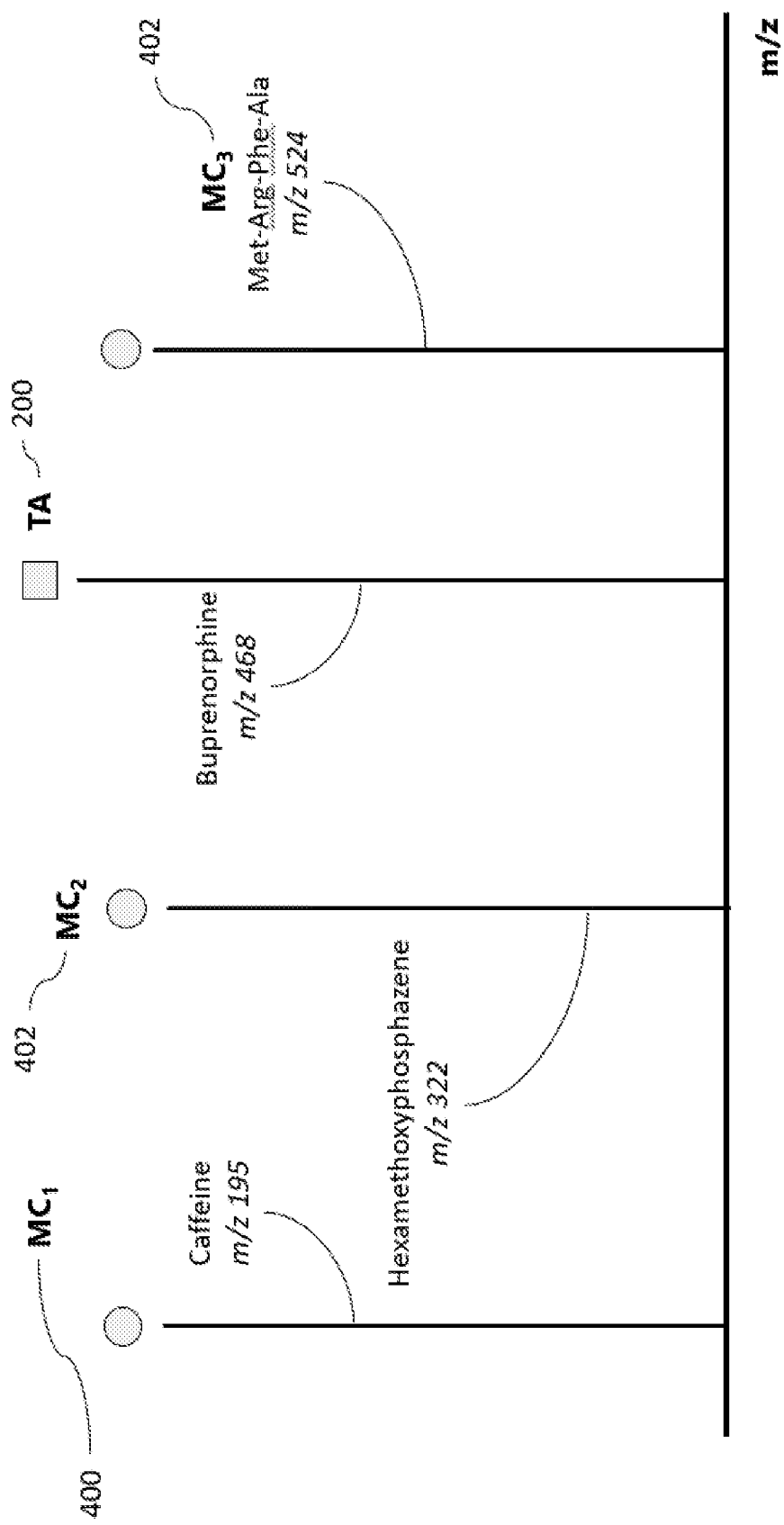
FIG. 5 exemplifies the mass spectra of buprenorphine (m/z 468) as the target analyte extracted from human urine samples when using caffeine (m/z 195), hexamethoxyphosphazene (m/z 322) and Met-Arg-Phe-Ala (m/z 524) as molecular calibrants, according to an embodiment of the present disclosure.

FIG. 5 exemplifies the mass spectra of buprenorphine (m/z 468) as the TA 200 extracted from human urine samples when using caffeine (m/z 195, $MC_1$, 400), hexamethoxyphosphazene (m/z 322, $MC_2$, 402), and Met-Arg-Phe-Ala (m/z 524, $MC_3$, 404) as molecular calibrants (MC). The MCs were deposited in one of the loading zones 108 to correct for potential drifts and/or changes in the instrumental response, such is the case for high-resolution instruments or ion mobility instruments because of changes in the humidity and temperature among other environmental factors. In combination with a MEC 202, either on the same loading zone 108, or independent loading zone 106, it is possible to execute both correction for potential drifts in the ion mobility-time/exact-mass of the TA and sample-device unequivocal identification.

Figure 6:
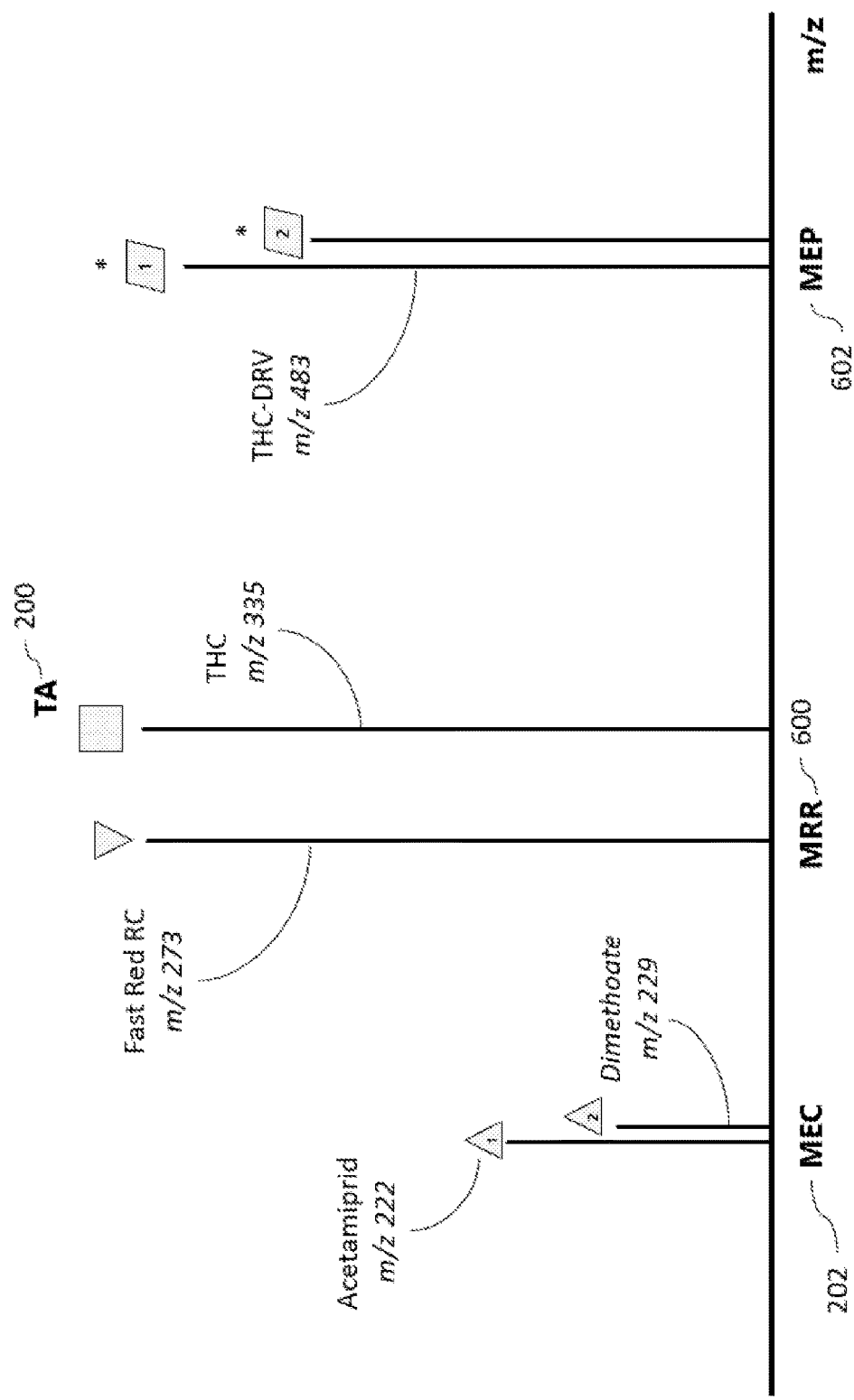
FIG. 6 portrays the mass spectra of THC (m/z 335), as the target analyte, extracted from saliva samples, when using acetamiprid (m/z 222) and dimethoate (m/z 229) as the molecular encrypted code, Fast Red RC (5-chloro-2-methoxybenzenediazonium salt) as the molecular reactive reagent, and THC-derivative (THC-DRV) as the molecularly encoded product, according to an embodiment of the present disclosure.

FIG. 6 portrays the mass spectra of THC (m/z 335) as the TA 200 extracted from saliva samples when using acetamiprid (m/z 222) and dimethoate (m/z 229) as the MEC 202, Fast Red RC (5-chloro-2-methoxybenzenediazonium salt) as the MRR 600, and THC-derivative (THC-DRV) as the MEP 602. The MEC was pre-loaded in one of the depressions/protrusions 108 on the molecular cryptographic sampling device 10. The TA was collected on the sampling zone 104 by placing a droplet of 10 μL of human saliva on top of the coated area for 5 minutes. The MRR is delivered on the elution/ionization fluid (e.g., methanol:water, 95:5, 0.1% formic acid). After a given interaction time, TA and MRR generate a MEP which may be seen in the MS data when performing the instrumental analysis.

The elution of the TA 200 and MT 202 from the molecular cryptographic sampling device 10 may be performed via liquid, laser, or thermal desorption. Some of the workflows herein described include the use of chromatographic instrumentation to aid resolving molecules of interest potentially co-extracted on the sampling device and with the same mass to charge ratio (e.g. isobars or isomers). In some preferred examples, the molecular cryptographic sampling device 10 herein described may be directly interfaced to mass spectrometry instrumentation using technologies such as, but not limited to, LESA, OPSI, DOS, DBDI, DESI, DART, Mass Spec-Pen, or combinations thereof. Likewise, the molecular cryptographic sampling device 10 may be directly interfaced to mass spectrometry instrumentation, without additional instrumentation via substrate-ESI, such as is the case with coated blade spray, enhanced coated blade spray, or magnetic blade spray.

In some examples, the elution of multiple TA and MEC from a molecular cryptographic sampling device 10 by immersing the molecular cryptographic sampling device 10 in a vessel containing in a fixed volume of an elution solvent. After analyte desorption, an aliquot of the elution solvent containing the TA and the MEC is transferred to the liquid chromatography (LC) system for analysis. Separation of the analytes allows for unequivocal identification of the TA and the MEC based on retention times. After analyte separation, TA and MEC are detected by either a fluorescence detector, a refractive index detector, or a diode array detector. In some examples, the LC system is interfaced to a Mass Spectrometry instrument. In preferred examples, the mass spectrometry system is a triple quadrupole and allows obtaining tandem mass spectrometry data besides retention time information. Other high-end mass spectrometry systems may also be used to obtain further information including, but not limited to, orbitrap, time of flight, quadrupole time of flight, and ion cyclotron. Likewise, a person skilled in the art would comprehend that other separation technologies such as ion mobility analyzers would further enhance the selectivity by adding additional information (i.e. drift time) about the TA(s) and MEC. Examples of ion mobility analyzers include differential mobility (DMS), trapped ion mobility spectrometry (TIMS), travel wave ion mobility (TWIMS), structural for lossless ion manipulations (SLIM), drift tube, and high-field asymmetric waveform ion mobility spectrometry (FAIMS).

In some examples, the elution of TA and MEC from a molecular cryptographic sampling device 10 using thermal desorption. TA and MEC elution is performed by inserting the molecular cryptographic sampling device 10 either on a thermal desorption unit (TDU) or the injection port liner of a gas chromatography (GC) instrument. By applying high temperature and a flow of gas, TA and MEC are eluted from the molecular cryptographic sampling device 10 and transferred into the GC column for separation. After analyte separation, TA and MEC are detected by a flamer ionization detector (FID), a nitrogen phosphorus detector (NPD), an electron capture detector (ECD), a thermal conductivity detector (TCD), a flame photometric detector (FPD), a photoionization detector (PID), or an electrolytic conductivity detector (ELCD). In some examples, the LC system is interfaced to a Mass Spectrometry instrument. In preferred examples, the mass spectrometry system is a quadrupole-orbitrap which allows obtaining tandem mass spectrometry data in high resolution besides retention time information. It will be understood that other high-end mass spectrometry systems may also be used to obtain further information including, but not limited to, triple quadrupole, time of flight, quadrupole time of flight, and ion cyclotron. Likewise, a person skilled in the art would comprehend that other ion separation technologies, such as ion mobility analyzers, would further enhance the selectivity by adding additional information (i.e. drift time) about the TA(s) and the MEC. Examples of ion mobility analyzers include differential mobility (DMS), trapped ion mobility spectrometry (TIMS), travel wave ion mobility (TWIMS), structures for lossless ion manipulation (SLIM), drift tube, and high-field asymmetric waveform ion mobility spectrometry (FAIMS). In some particular examples, injection of the molecular cryptographic sampling device 10 into the injection port of the GC system is performed using a robotic arm.

Figure 7:
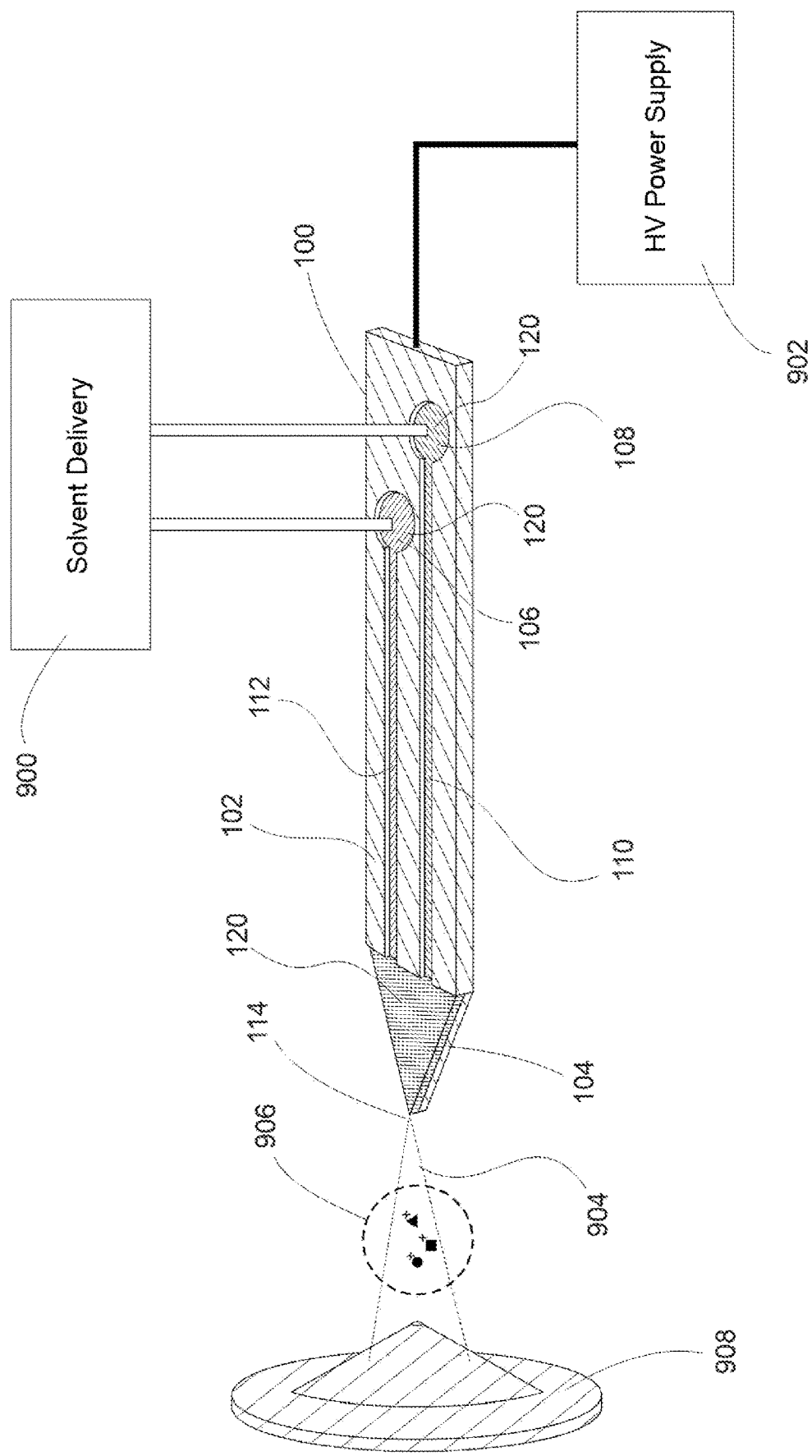
FIG. 7 presents the elution of target analyte and molecular encrypted code from the molecular cryptographic sampling device as an electrospray ionization solid-substrate, according to an embodiment of the present disclosure.

FIG. 7 presents the elution of the TA and MEC from the molecular cryptographic sampling device 10 as a solid-substrate ESI. Essentially, after TA collection on the loading zone 104, a fixed or a continuous amount of elution/ionization solvent is added to the loading zones 106 and 108 using a solving delivery system 900, causing the elution of the MEC and MIS from their respective coated substrates. Movement of the elution solvent towards the guided channels 110 and 112 towards the loading zone 104 leads towards the elution of the TA. After an interaction time (e.g., 10 seconds), a high-voltage supply 902 is turned on and high-voltage is applied to the non-coated area 100 of the substrate 102, then generating an electrospray cone 904 at the tip 114 of the substrate 102. Ions 906 are expelled from the molecular cryptographic sampling device 10 and transferred to the MS inlet 908 for analysis. In preferred examples, the mass spectrometry system is a time of flight MS allows obtaining high resolution mass spectrometry data 910. Other high-end mass spectrometry systems may also be used to obtain further information including, but not limited to, triple quadrupole, orbitrap, quadrupole time of flight, and ion cyclotron. Likewise, a person skilled in the art would comprehend that other ion separation technologies, such as ion mobility analyzers, would further enhance the selectivity by adding additional information (i.e. drift time) about the TA and MEC. Examples of ion mobility analyzers include the following: differential mobility (DMS), trapped ion mobility spectrometry (TIMS), travel wave ion mobility (TWIMS), structures for lossless ion manipulations (SLIM), drift tube, and high-field asymmetric waveform ion mobility spectrometry (FAIMS).

Figure 8A:
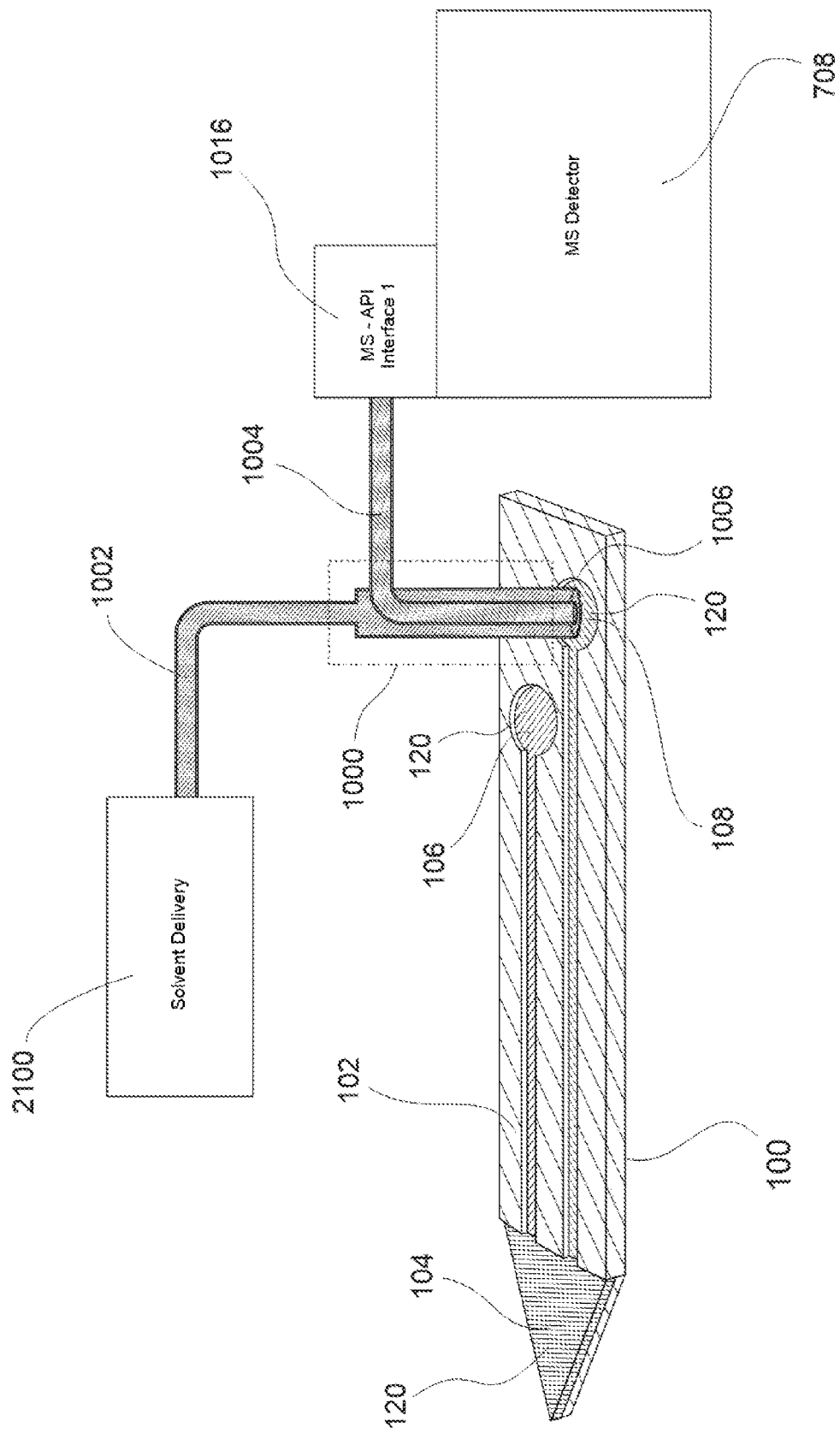
FIGS. 8 (a), 8(b), and 8(c) exemplify the elution of target analyte and molecular encrypted code from the molecular cryptographic sampling devices with either one liquid micro junction device or multi-liquid micro junction device for spatially resolved elution of target analyte, molecular encrypted code, and molecular reactive reagent, according to an embodiment of the present disclosure.
Figure 8B:
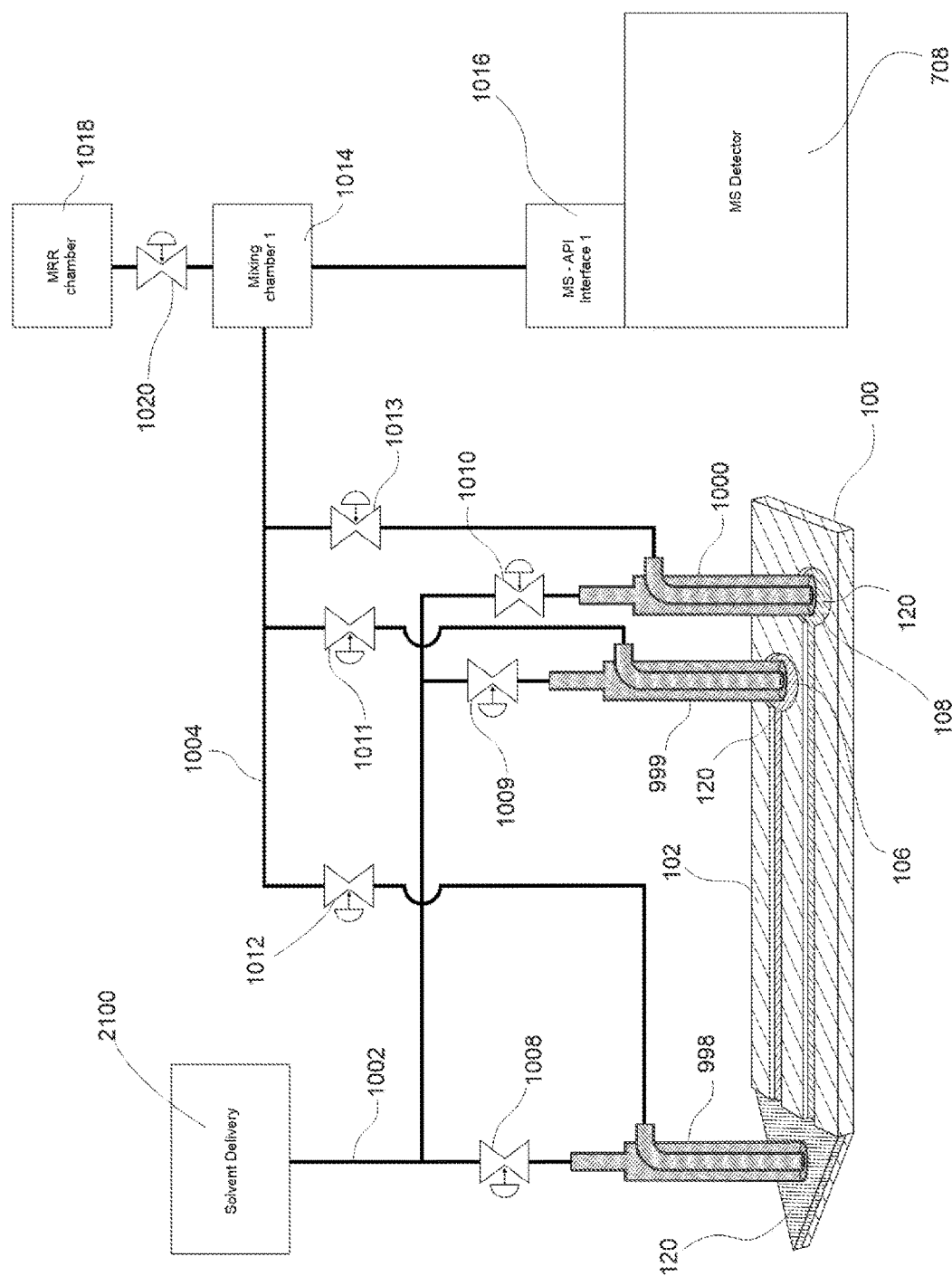
Figure 8C:
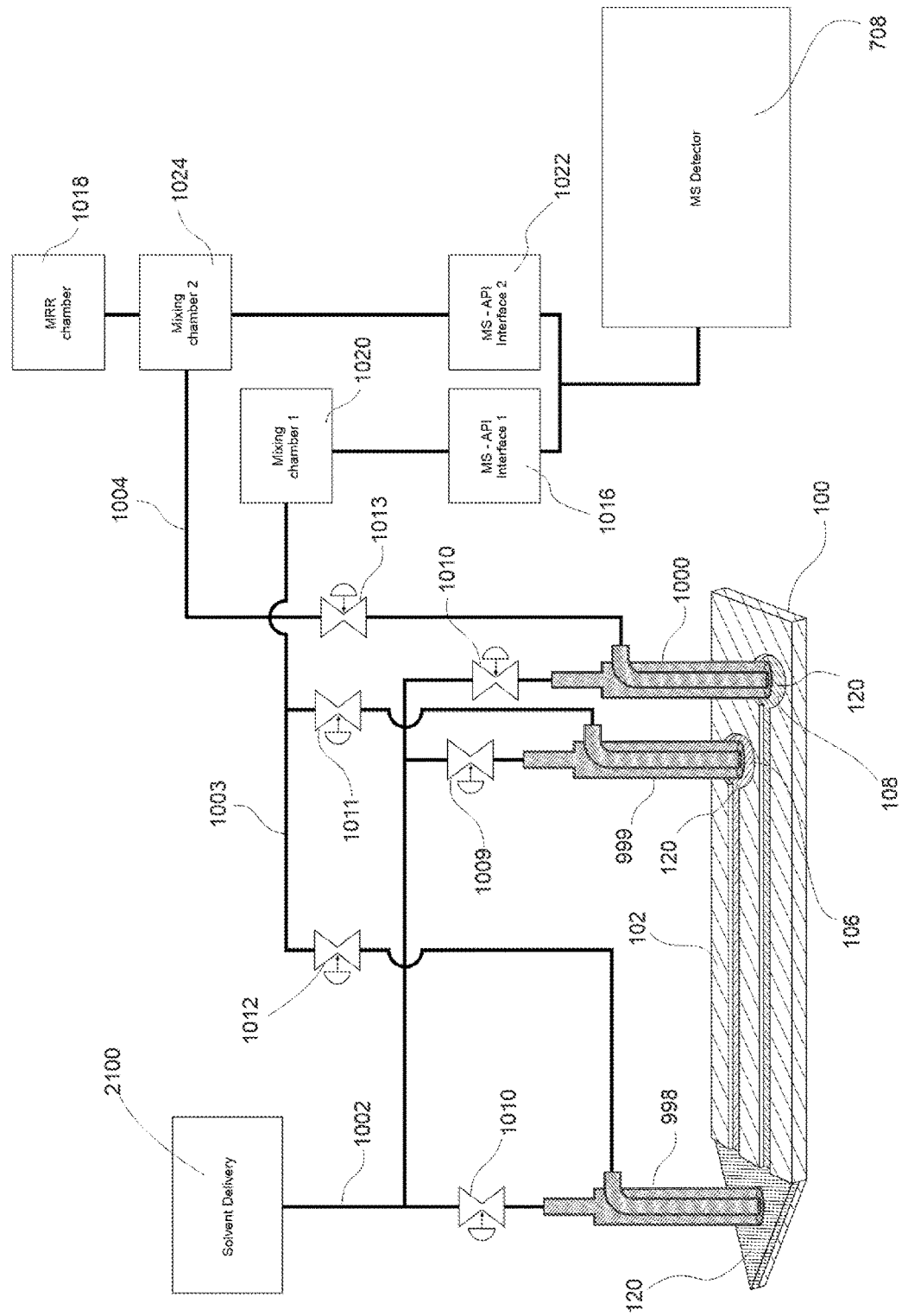

FIG. 8(a) exemplifies the elution of the TA and MEC from the molecular cryptographic sampling device 10 with one liquid micro junction (LMJ) device. FIGS. 8(b) and 8(c) exemplify elution of the TA and MEC from the molecular cryptographic sampling device 10 with multi-liquid micro junction (LMJ) devices for spatially resolved elution of TA, MEC and MRR. The LMJ probe 1000 is composed of an organic solvent delivery device 2100 and a solvent delivery duct 1002 and an annulus pick-up solvent duct 1004. Dimensions of the LMJ probe have been extensively described in the literature. When in contact with a surface the LMJ probe generates a junction 1006. In some examples, a single LMJ probe is used to desorb the TA and MEC from the loading zones 104, 106, and 108. In such examples, the LMJ is interfaced to the MS system 708 using an atmospheric pressure interface (API) 1016. Examples of API include, but are not limited to, ESI, atmospheric pressure photon ionization (APPI) and atmospheric pressure chemical ionization (APCI). In some preferred examples, as presented in FIGS. 8(b) and 8(c), multiple LMJ probes 998, 999, and 1000 may be used to desorb the TA and the MEC from the loading zones 104, 106, and 108, respectively. In particular examples, TA, MIS, and IDT are stored in different loading zones of the molecular cryptographic sampling device 10. In such example, the analyst may perform spatially resolved elution of either the TA, the MIS or IDT, by controlling a set of valves 1008, 1009, and 1010. Likewise, the method may be configured to selectively transport either the TA, the MIS or IDT towards the API 1016 by a set of valves 1011, 1012, and 1013. In this particular example, exemplified by FIG. 8(b), the effluents of the multi-LMJ device may be confined on a mixing chamber 1014, prior to the transfer of the TA, MTs, and any byproducts to the MS system 708 using an API interface 1016. In some particular examples, exemplified by FIG. 8(b), an MRR may be added on-line to the system using a delivery system 1018 and the amount of standard delivered can be controlled using a valve 1020. In a particular set of experiments, exemplified by FIG. 8(c), multiple LMJ probes are used to desorb the TA and the MEC from the loading zones 104, 106, and 108, respectively. In addition, the LMJ devices 998, 999, and 1000 are interfaced to the MS using multiple atmospheric pressure interfaces 1016 and 1022. In a preferred example, elution transportation and interface with the MS system 708 of the IDT is performed in a separate fashion from the TA and the MIS. In that particular experiment, the IDT are mixed with an MRR 1018 in a separate chamber 1024, prior to the API 1022, to generate a MEP. The TA and other MP collected in zones 104 and 106 may be discretely desorbed and sent to a separate chamber 1026, prior to its transfer to the API 1016. Micro-liquid elution from the substrate 100 on the molecular cryptographic sampling device 10 may be performed using other technologies such as mass-spec pen, nano-desorption electrospray ionization (nano-DESI), and liquid extraction surface analysis (LESA), among others.

Figure 9:
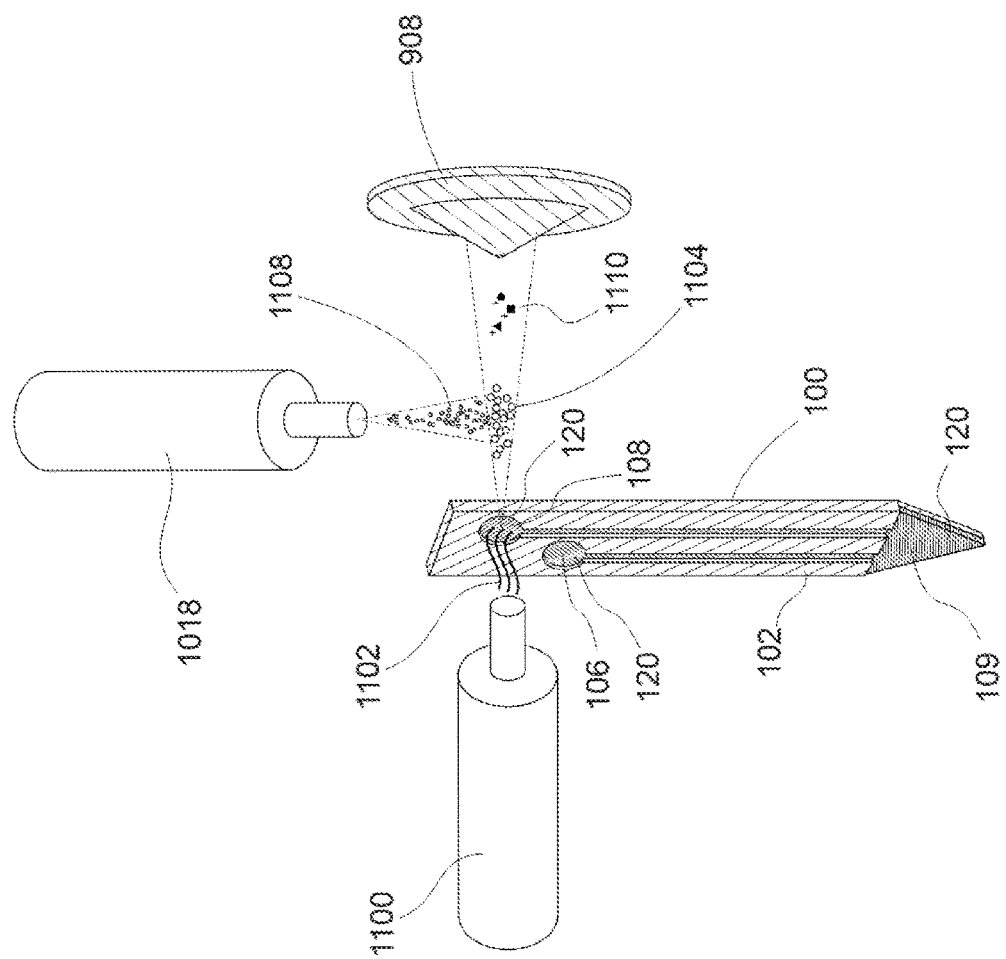
FIGS. 9(a) and 9(b) present the elution of target analyte and molecular encrypted code from the molecular cryptographic sampling device using a standalone mass spectrometer in combination with an ambient mass spectrometry technology based on thermal elution of the analytes, according to an embodiment of the present disclosure.
Figure 10A:
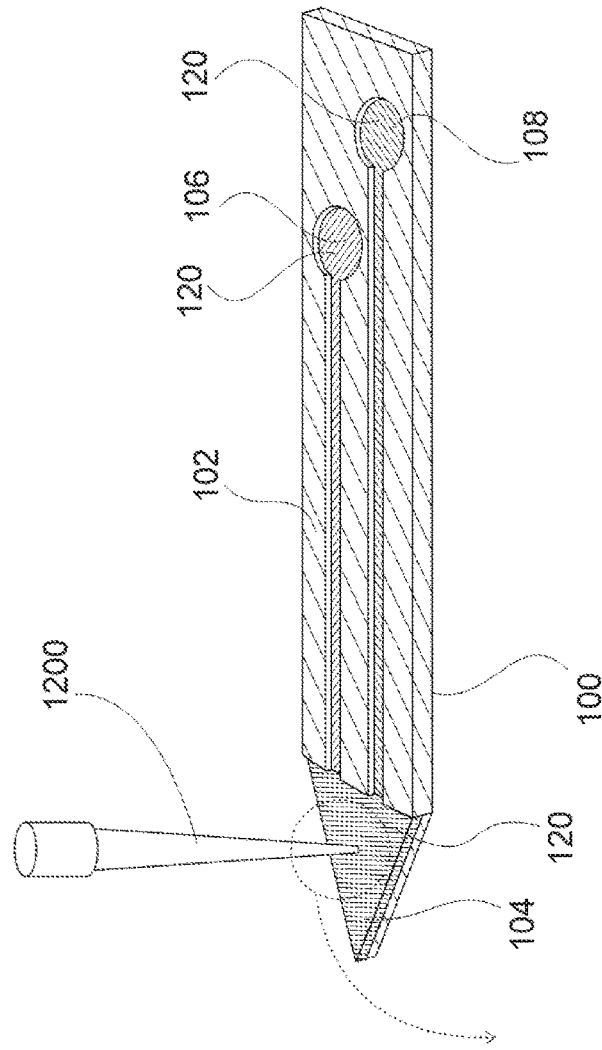
FIG. 10 illustrates the elution of target analyte and molecular encrypted code from the molecular cryptographic sampling device using a standalone mass spectrometer in combination with an ambient mass spectrometry technology such as liquid extraction surface analysis, according to an embodiment of the present disclosure.
Figure 10D:
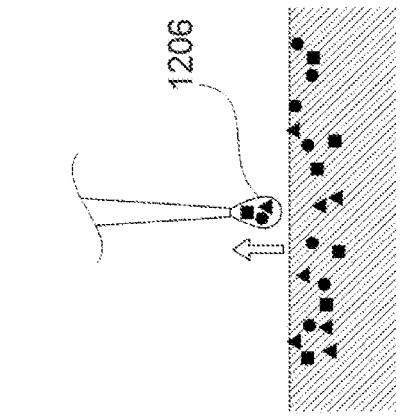
Figure 10C:
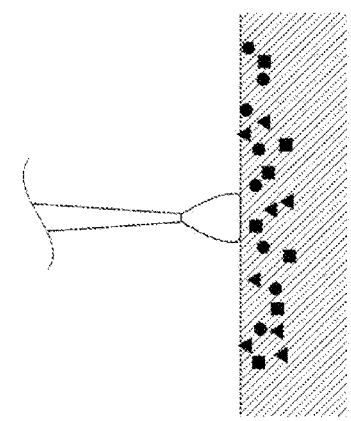
Figure 10B:
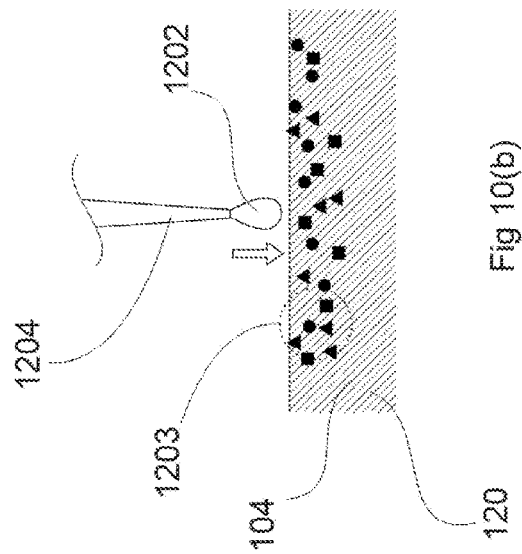
Figure 11:
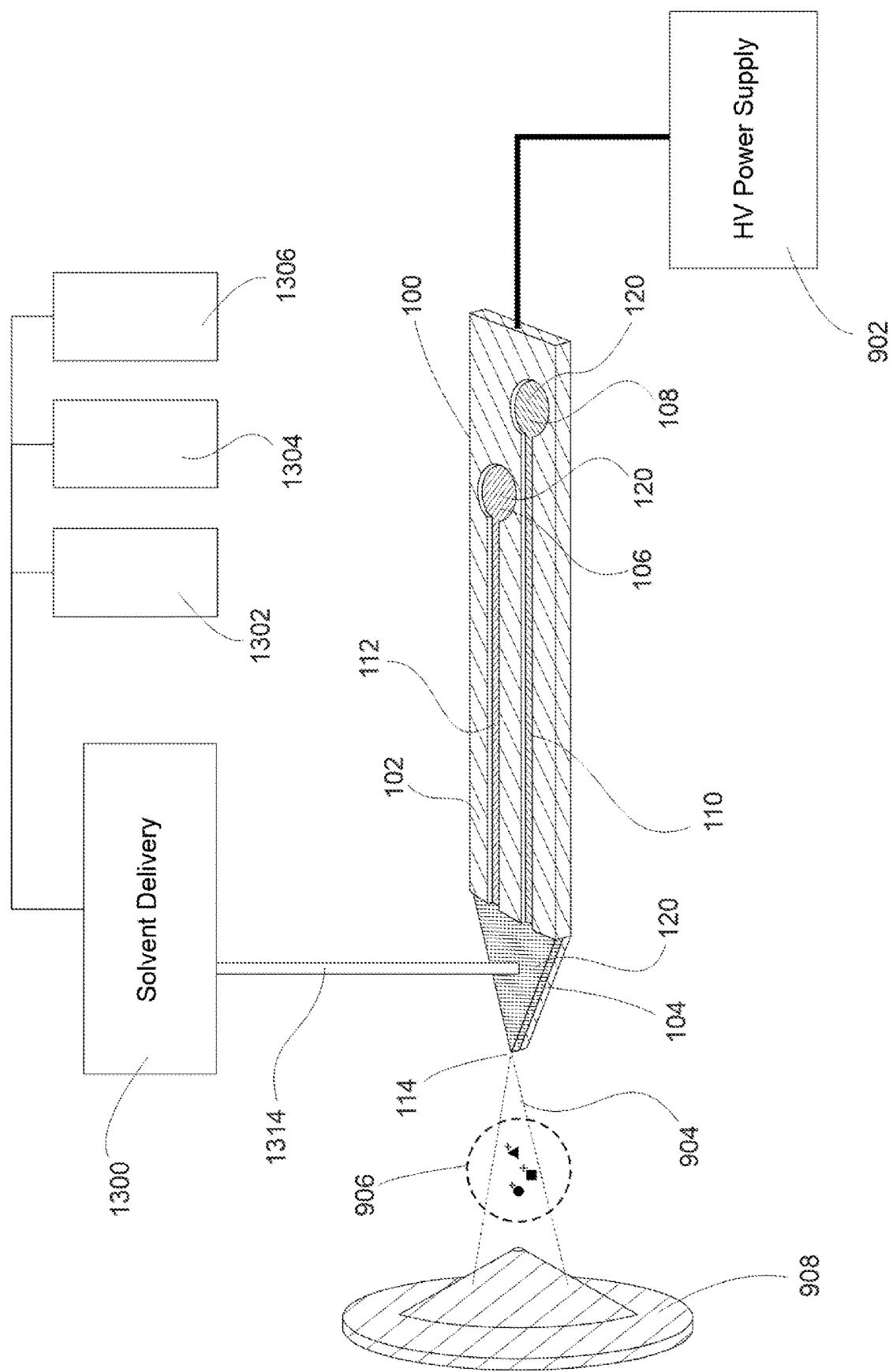
FIG. 11 depicts a pumping device for selective elution of target analyte from the molecular cryptographic sampling device, according to an embodiment of the present disclosure.

FIG. 9 presents the elution of TA and MEC from the molecular cryptographic sampling device 10 using a stand-alone mass spectrometer in combination with an ambient mass spectrometry technology based on thermal elution of the analytes. Examples of thermal elution include, but are not limited to, DART, DOS, TD-ESI, flowing atmospheric-pressure afterglow (FAPA), low temperature plasma (LTP), and DBDI. In a preferred example, an ambient mass spectrometry interface with a well-defined desorption pattern (<3 mm) 1100, such as DART or DOS, is used for the selective elution of the TA and MEC from the different loading zones 104, 106, 108. Essentially, a beam of heated gas with highly activated ionization species 1102 interacts with a loading zone 108 causing the elution of such analytes 1104 with a low enough vapor pressure to be carried out onto the gas phase. Subsequently, molecules of interest travel towards the MS inlet 908 for analysis. In preferred examples, the mass spectrometry system is a time of flight MS allows obtaining high resolution mass spectrometry data. Other high-end mass spectrometers may also be used to obtain further information of the sample under scrutiny, including, but not limited to, triple quadrupole, orbitrap, quadrupole time of flight, and ion cyclotron. Likewise, a person skilled in the art would comprehend that other ion separation technologies, such ion mobility analyzers, would further enhance the selectivity by adding additional information (i.e., drift time) about the TA(s) and the MEC. Examples of ion mobility analyzers include the following: differential mobility (DMS), trapped ion mobility spectrometry (TIMS), travel wave ion mobility (TWIMS), structures for lossless ion manipulations (SLIM), drift tube, and high-field asymmetric waveform ion mobility spectrometry (FAIMS). Likewise, it will be understood that the rationale for using ambient ionization interfaces with well-defined elution resolution is to independently and timely introduce the molecules of interest named TA, MC, MIS and IDT to the MS system. Also, elution of the molecules of interest from the loading zones, with defined time and spatial resolution, can be attained via liquid desorption. Examples of liquid elution with well-defined resolution include, but are not limited to, DESI, nano-DESI and OPSI. In some preferred examples, an MRR in the traveling path of the ions 1104 towards the MS inlet. An MRR chamber 1018 with a delivery valve 1020 can be used to set the amount of MRR to be released orthogonal to the ion path. After a few milliseconds, TA and/or MEC react with the MRR molecules 1108 to generate a MEP 1110 under ambient conditions.

FIG. 10(*a*) illustrates the elution of TA and MEC from the molecular cryptographic sampling device 10 using a stand-alone mass spectrometer in combination with an ambient mass spectrometry technology such as LESA 1200. In this example a droplet of the elution liquid 1202 is delivered to the loading zone 104 using a pipette tip 1204 (step 1) to collect analytes 1205 (step 1, FIG. 10(*b*)). After a defined contact time (FIG. 10(*b*)), the droplet containing the analytes 1206 is withdrawn onto the pipette tip 1204 (FIG. 10(*d*)) and transported to a nano-ESI chip for ionization of the TA (step 2). The droplet containing the molecules of interest is deposited on the nano-ESI emitter and, by applying a high potential difference between the nano-ESI emitter and the MS-inlet, an ESI cone is generated and ions of the molecules of interest are expelled toward the instrument so to generate mass spectrometry data. The LESA system allows for better sensitivity by providing the following features: longer elution times from the coated substrate (i.e., more analyte collected on a small volume), well-defined ionization substrate with minimal evaporation (i.e., nano-ESI vessel), and best ESI ionization and transmission provided by intrinsic properties of nano-ESI. In this example, where multiple loading zones are used (104, 106, 108), the analyst may selectively and timely elute and ionize the TA, MC, MIS, and IDT. Likewise, an MRR may be present on the elution droplet 1202 for generation of MEP with either the TA or the MRT. The micro-amount of solvent used to elute the MT and TA from the substrate may also be interfaced with a variety of analytical instrumentation including gas chromatography, liquid chromatography, and any ionization interface directly coupled to a stand-alone instrument. Examples of ionization interfaces directly couple to mass spectrometry instrumentation would include, but are not limited to, DART, OPSI, DESI, DBDI, and TD-ESI.

Figure 13:
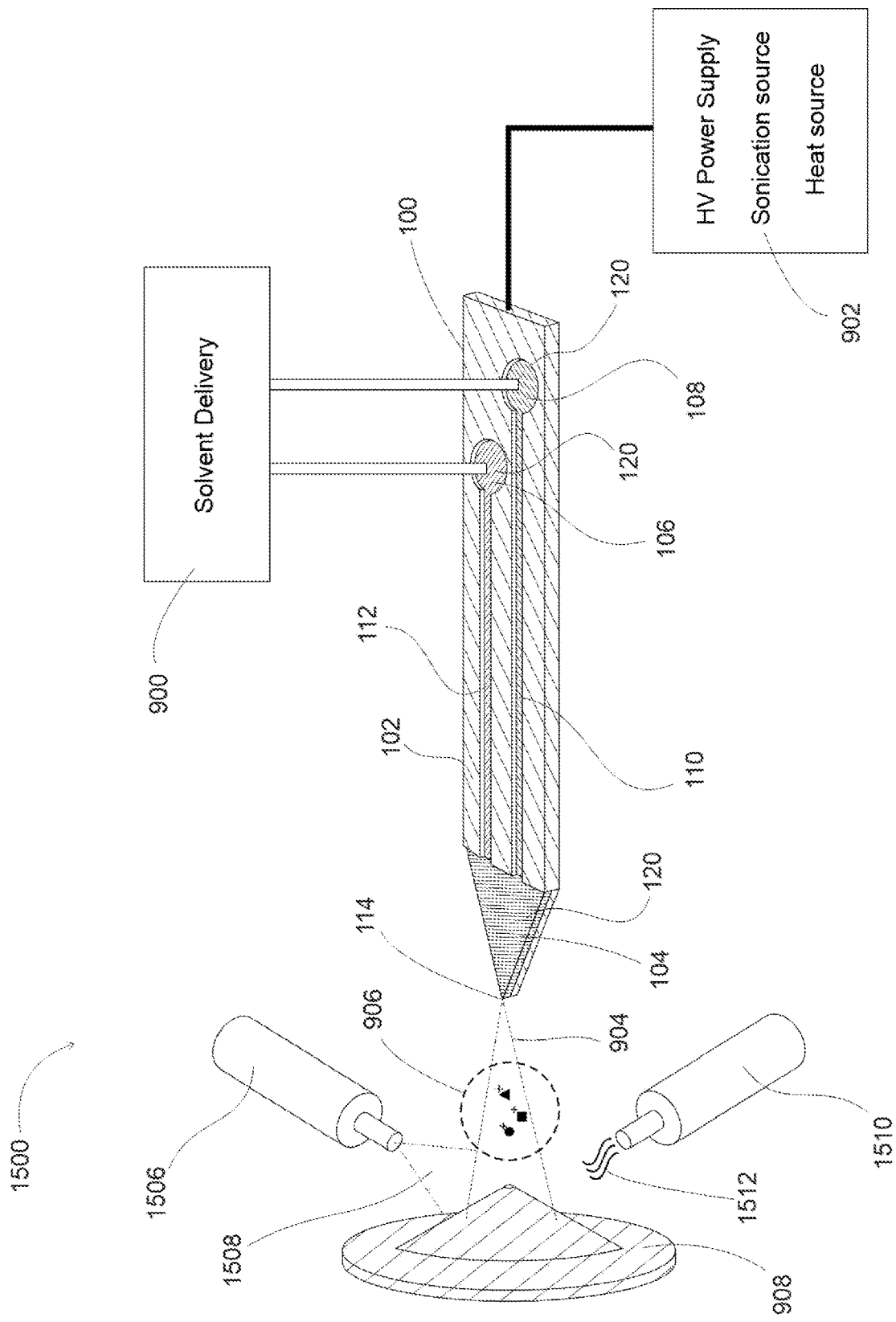
FIG. 13 presents a schematic of a mass spectrometry interface for the molecular cryptographic sampling device, according to an embodiment of the present disclosure.

FIG. 13 depicts a pumping device 1300 for selective elution of TA from a molecular cryptographic sampling device 10. In this example, different elution solvents 1302, 1304, 1306 may timely be delivered on the loading zone 104 of the molecular cryptographic sampling device 10, 100 to generate different mass spectra profiles depending on the composition of the elution solvent. It should be clear to a person skilled in the art that the solvent delivery system 1300 may be used to mix different elution solvents and study selective elution of the target analytes. Likewise, the elution solvent may be deposited in the different loading zones using a robotic arm guided probe 1314. Examples of spatially resolved elution of surface include, but are not limited to, LESA, OPSI and nano-DESI. In preferred examples, the molecular cryptographic sampling device 10 is used as a coated blade spray system. In such examples, the solvent delivery system distributes finite amounts of the different elution solvents 1302, 1304, 1306 timely. Thus, by applying a high voltage 902 to the molecular cryptographic sampling device 10, 100 a Taylor cone 904 is generated at the tip of the substrate 114 expelling ions 906 of the mass spectrometer inlet 908 to generate a mass spectra profile. By selective adding finite amounts of the elution solvent 1304 and 1306, different mass spectra profiles may be attained. One or more elution solvents may contain an MRR that interacts with either the TA or the MEC to generate a MEP. Likewise, a person having ordinary skill in the art would understand that one may perform multiple elutions from a given loading zone 106, 108 with multiple elution solvents as long as the analyte has not been depleted from the polymeric sorbent. In some examples, solvent combinations can be used to favored either the elution of more polar or more hydrophobic molecules.

Figure 12:
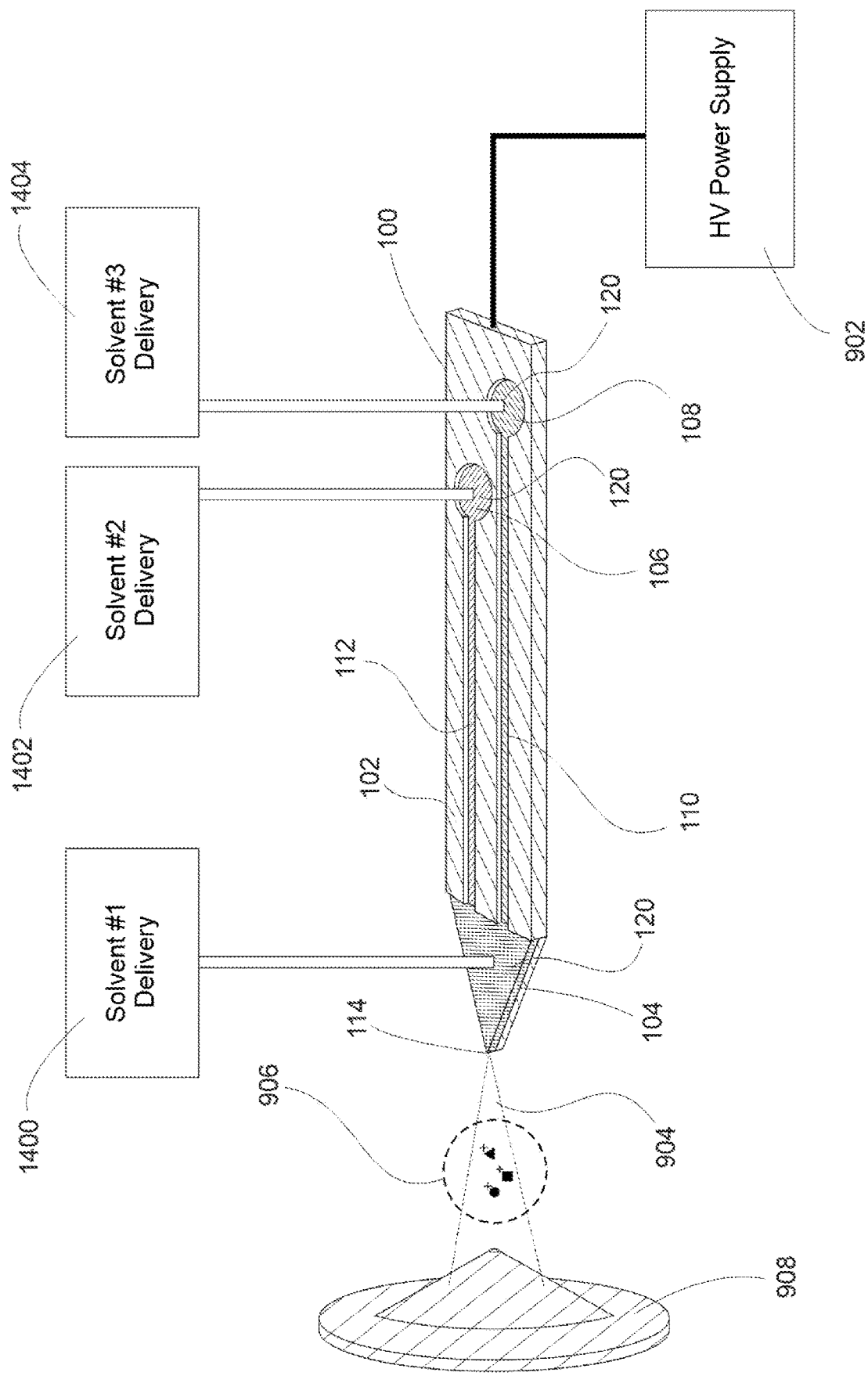
FIG. 12 presents the spatially resolved elution of target analyte(s) and molecular encrypted code from the molecular cryptographic sampling device as a electrospray ionization solid-substrate, according to an embodiment of the present disclosure.

FIG. 12 presents the elution of the TA and MEC from the molecular cryptographic sampling device 10 as a solid-substrate ESI. A set of pumping systems 1400, 1402, 1404 is used to discretely elute the TA, MEC, and MRR/MC selectively deposited in the different loading zones 104, 106, 108. Elution of the molecules of interest may be performed concomitantly or in a time basis. In some examples, elution of the analytes of interest is performed using the same solvent composition. In some preferred examples, different elution solvents are used at the different loading zones.

FIG. 13 presents a schematic of a mass spectrometry interface 1500 for molecular cryptographic sampling device 10, 100. The system is composed of a clamping system 902 which may provide high voltage, sonication/vibration, and heat to the molecular cryptographic sampling device 10, 100. Similarly, the system has a solvent delivery system 900 which may provide single or multiple combinations of elution solvents to elute TA or MTs from the loading zones 104, 106, 108. Furthermore, the interface includes a discrete and independent cleaning device 1506 that may deliver a cleaning solvent between experiments with the objective of removing any potential molecules or contaminants adhered to the surface of the MS inlet 908. The device 1506 may also be used to deliver MRR 1508 on the gas phase trajectory of the analytes of interest 906 in order to generate MEP. An additional feature of the interface 1500 is an independent heated nebulizer 1510 that may be used to further enhance the generation of smaller droplets by providing a heated gas 1512 and, consequently, enhance ion transmission into the MS inlet 908.

Figure 14:
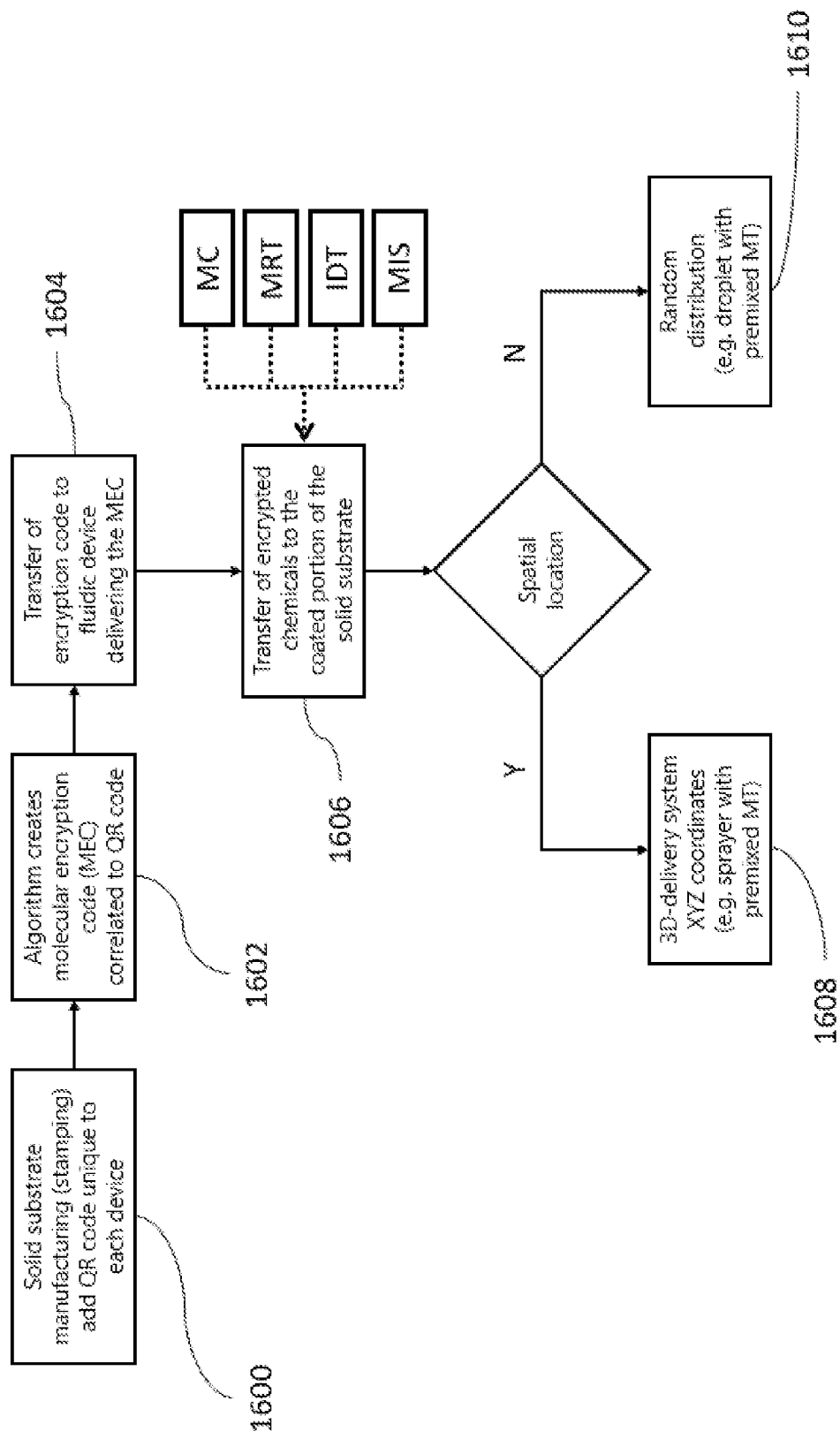
FIG. 14 illustrates a workflow for encrypting molecular information on molecular cryptographic sampling devices when the molecular encrypted code is introduced post coating manufacturing, according to an embodiment of the present disclosure.

FIG. 14 illustrates the workflow for encrypting molecular information on molecular cryptographic sampling devices 10 when the MEC is loaded on the coated substrate post-coating manufacturing. In the first step 1600, a substrate 102, preferably made of a conductive material, is made to a well-defined size and geometry (e.g., via stamping or photoetching) and subsequently is labelled/engraved/embossed with indicia such as a quick read code (QRC), and coated with a polymeric sorbent on a portion of the substrate 102 by a robotic system. Subsequently, a computer system 1602 generates a combination of MTs that comprise the MEC (i.e., amounts of MTs, class of MTs, and number of MTs) which is unique to each sampling device. In the next step 1604, the MEC is transferred to the firmware of the fluidic system. Then, based on the MEC, the fluidic system 1606 prepares the amounts of MC, MRT, IDT, and MIS. Depending on whether spatial resolution is needed or not, the MC, MRT, IDT, and MIS that will be loaded on the substrate 102. MTs to be deposited on the coated substrate are dissolved in an organic solvent, such that the solvent delivery system may deposit a fix volume that corresponds to a given amount of MT. If the MTs do not need to be spatially resolved on the surface of the substrate 102 the MC, MRT, IDT are mixed and delivered using a solvent delivery system with a fixed location. Alternatively, if the molecular cryptographic sampling device 10 has multiple loading zones and the MTs need to be spatially resolved in said surface, the solvent delivery system may be mounted on an XYZ robotic arm 1608 which may be used to spatially deposit each of the MTs on the required loading zone.

Figure 15:
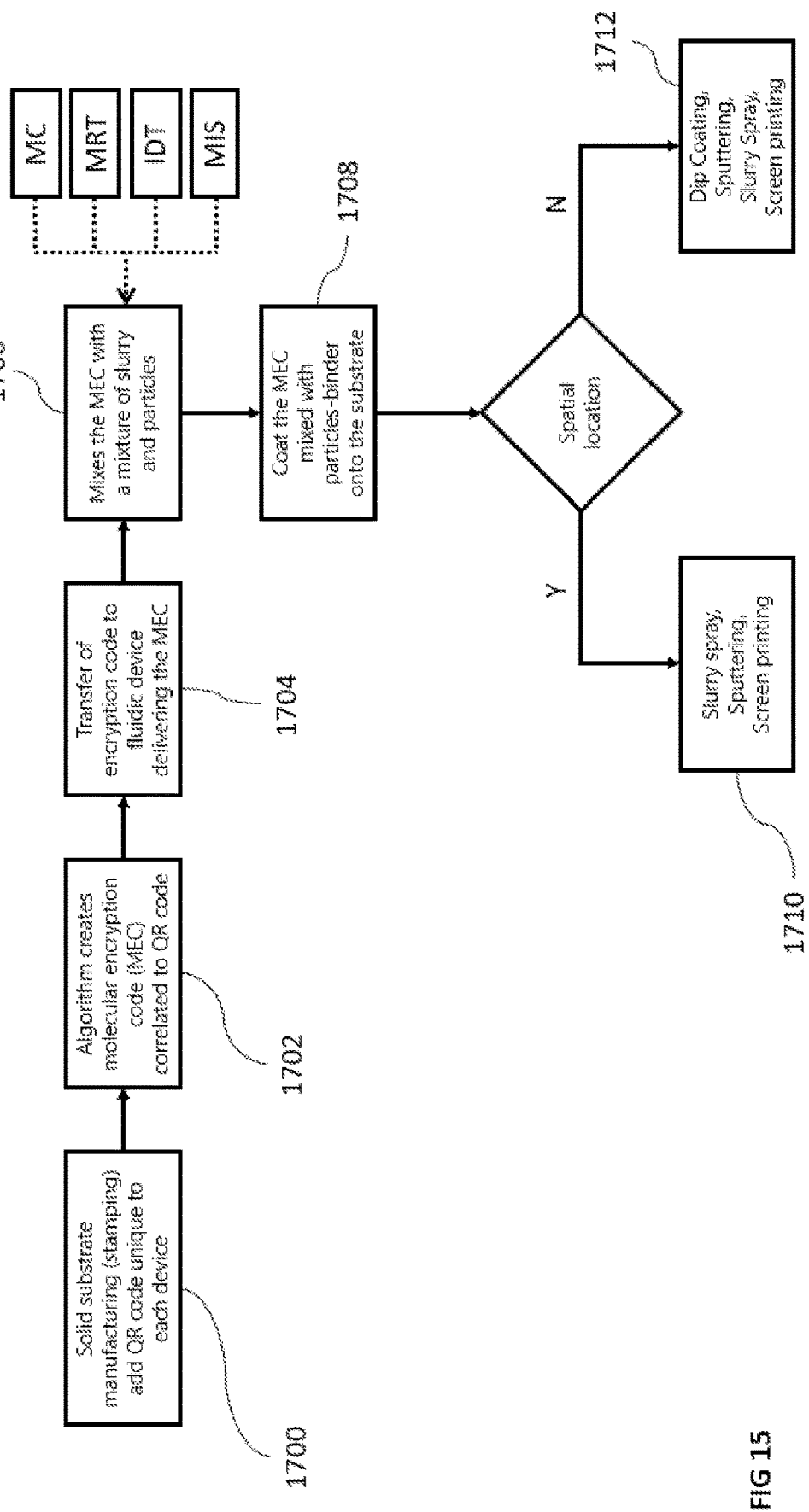
FIG. 15 illustrates a workflow for encrypting molecular information on molecular cryptographic sampling devices when the molecular encrypted code is introduced during coating manufacturing, according to an embodiment of the present disclosure.

FIG. 15 illustrates the workflow for encrypting molecular information on molecular cryptographic sampling devices 10 when the MEC is loaded onto the extractive material during coating manufacturing. In the first step 1700, a substrate 102, preferably made of a conductive material, is made to a well-defined size and geometry (e.g., via stamping or photoetching) and subsequently is labelled/engraved/embossed with indicia such as a QRC. Subsequently, a computer system 1702 generates a combination of MTs that comprise the MEC and such combination (i.e., amounts of MT, class of MT, and number of MT) is unique to each sampling device. In the next step 1704, the MEC is transferred to a fluidic system. Then, the fluidic system 1706 blends the required amounts of MC, MRT, IDT, and MIS based on the MEC and delivers them to a chamber for mixing with a slurry of particles and binder to be coated on the substrate 102. Subsequently, particles are coated on the solid substrate 1708. If the molecular cryptographic sampling device 10 contains multiple analyte loading zones and spatial resolution is needed 1710, particles may be deposited on specific areas of the substrate using spray coating, sputtering or screen printing, among others. If spatial resolution of the coating-MEC is not necessary, coating may be applied on the substrate 102 using dip coating, sputtering spraying, or screen printing 1712, among others.

Figure 16:
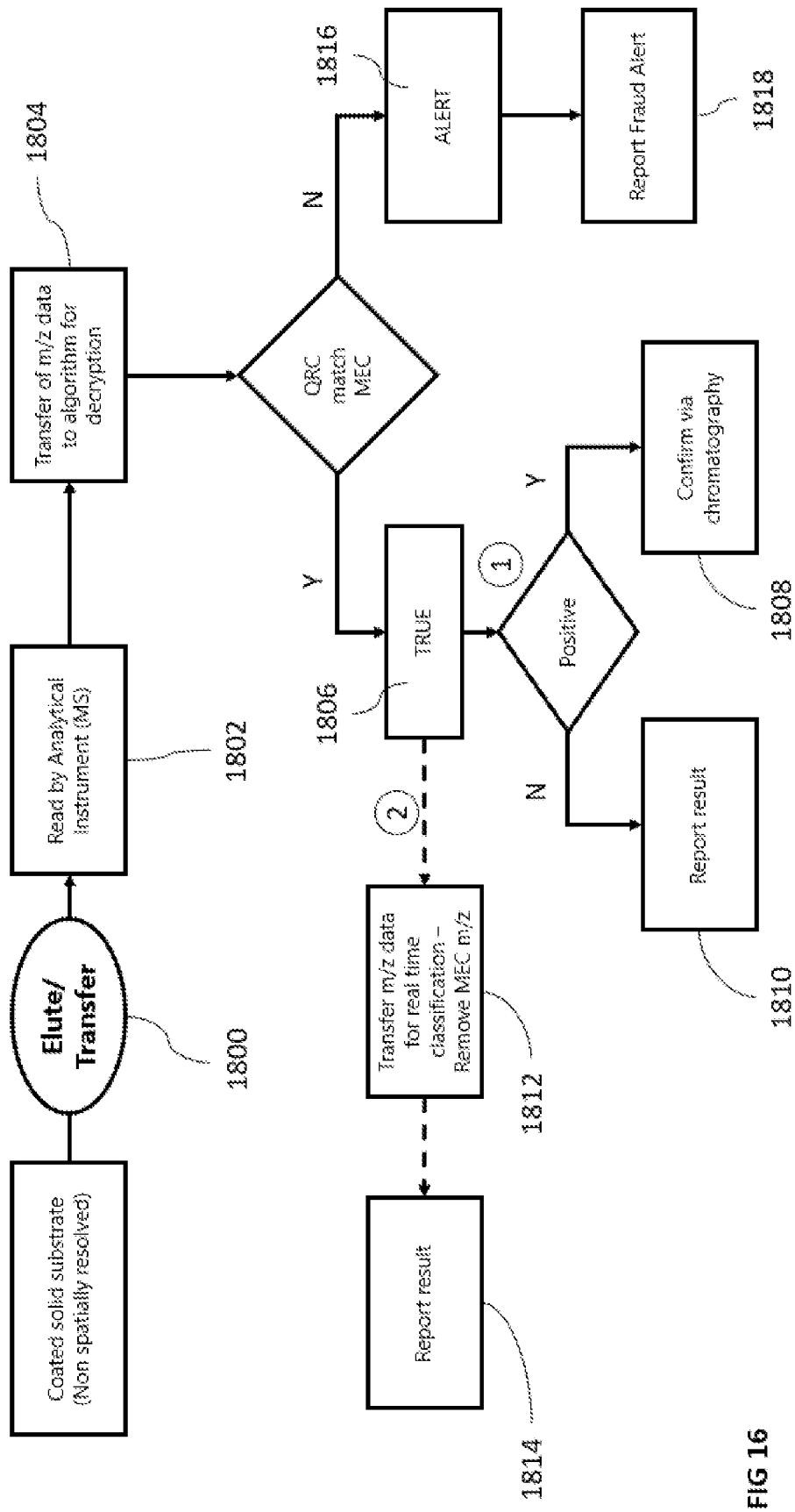
FIG. 16 exemplifies a workflow for deciphering molecular information on molecular cryptographic sampling devices when there is not spatial resolution of the target analyte and the molecular tag, according to an embodiment of the present disclosure.

FIG. 16 exemplifies the workflow for deciphering molecular information stored on molecular cryptographic sampling devices 10 when the TA and the MT are not spatially resolved on the substrate 102. First, the TA and MEC are eluted from the molecular cryptographic sampling device 10 and transferred to the analytical instrument 1800. Then, the TA and the MEC are read by the analytical instrumentation 1802. In some preferred examples, the instrumentation is a mass spectrometer. In the third step, the data generated is transferred to an algorithm 1804 for decryption. Then, the indicia on the substrate 102 is read by an optical device (e.g., a camera) and, if the information on the physical mark placed on the molecular cryptographic sampling device 10 matches the MEC 1806 stored on the molecular cryptographic sampling devices 10, it is confirmed the identity of the sample/device and the algorithm reports a "TRUE" value which allows for further examination of the sample. In one example, if there is a quantitative process and the result is positive and above the limits of quantitation of the method, the algorithm would suggest the analyst confirmation via separation technology such as liquid chromatography 1808. If there is a quantitative process and the result is negative, the algorithm would suggest reporting the negative results and continue with the following sample 1810. Alternatively, if the molecular cryptographic sampling devices 10 is used for a qualitative assessment of the sample (e.g., molecular profiling), the algorithm 1812 removes the signals of the MEC and other MT non-related to the sample, and transfers the data to a separate algorithm for real-time classification. Based on a data base previously built by the analyst, the classification algorithm 1814 determines the potential identity of the sample under scrutiny. In one example, exemplified in FIG. 18, the information on the indicia placed on the molecular cryptographic sampling device 10 does not match the MEC 1816. In such cases, the algorithm delivers a "FALSE" value prepares a report warning the analyst about a potential fraud 1818, and no further analysis of the sample is prepared.

Figure 17:
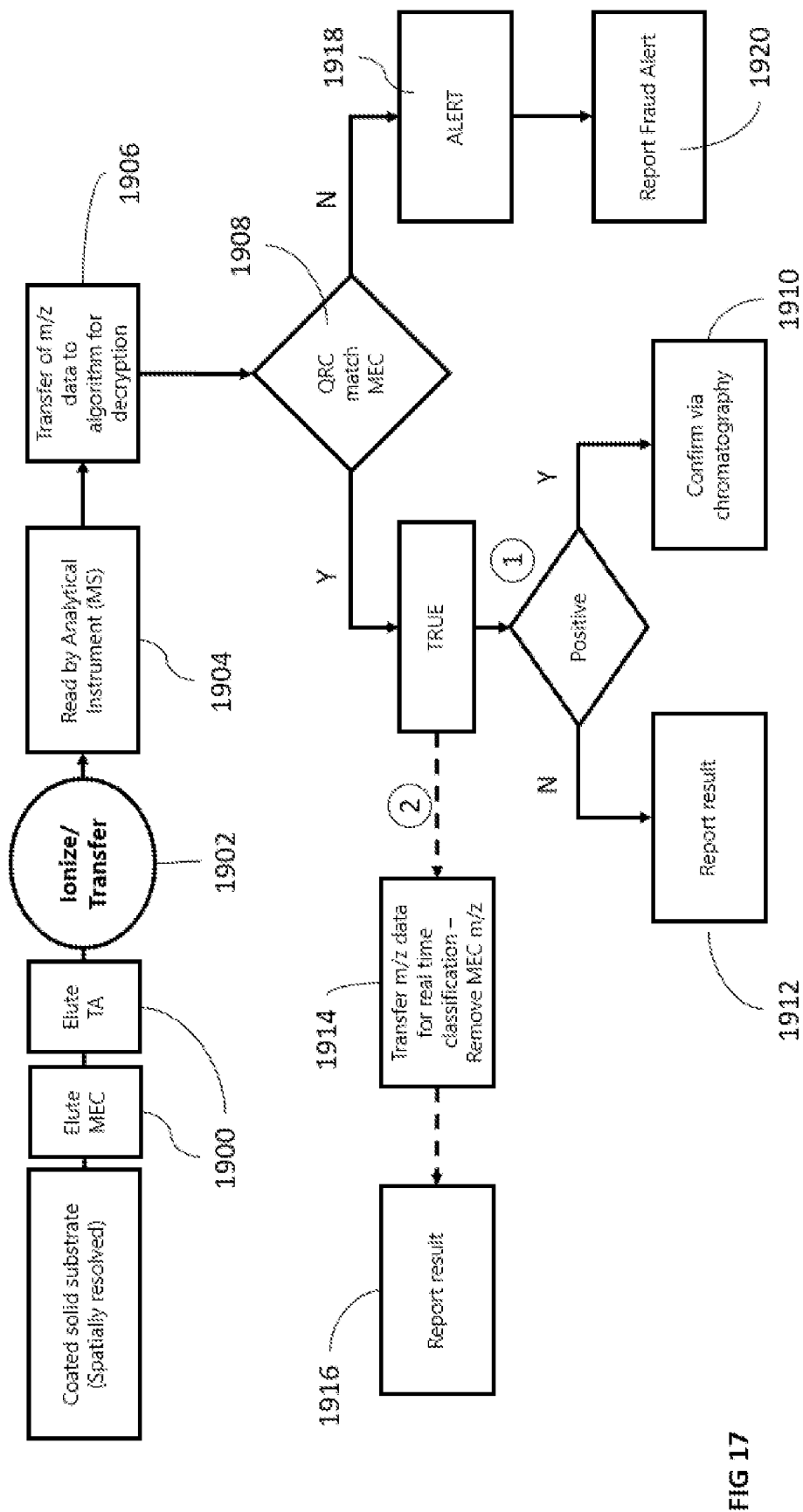
FIG. 17 represents a workflow for deciphering molecular information on molecular cryptographic sampling devices when there is spatial resolution of the target analyte and the molecular tag but the elution is executed concurrently, according to an embodiment of the present disclosure.

FIG. 17 represents the workflow for deciphering molecular information on molecular cryptographic sampling devices 10 when the TA and the MT are spatially resolved on the substrate 102 but the data collection in the instrument is executed concurrently. First, the TA and MEC are discretely eluted from the molecular cryptographic sampling device 10, 1900 and transferred concomitantly to the analytical instrument 1902. Subsequently, the analytes of interest are read by the analytical instrumentation 1904, preferably a mass spectrometer. Then, the indicia placed on the molecular cryptographic sampling device 10 is read by an optical device (e.g., a camera) and the data is transferred to an algorithm 1906 for decryption. If the information in the indicia placed on the molecular cryptographic sampling device 10 matches the MEC 1908 stored on the molecular cryptographic sampling device 10, the identity of the sample/device is confirmed and the algorithm reports a "TRUE" value which allows for further examination of the sample. In one example, if there is a quantitative process and the result is positive and above the limits of quantitation of the method, the algorithm would suggest the analyst confirmation via a separation technology such as liquid chromatography 1910. If there is a quantitative process and the result is negative, the algorithm would suggest reporting the results and continue with the following sample 1912. Alternatively, if the molecular cryptographic sampling device 10 is used for a qualitative assessment of the sample (e.g., molecular profiling), the algorithm 1914 removes MEC and other MT non-related to the sample and transfers the data to a separate algorithm for real-time classification. Based on a database previously build by the analyst, the classification algorithm 1916 determines the potential identity of the sample under scrutiny. In one example, exemplified in FIG. 17, the information in the indicia placed on the molecular cryptographic sampling device 10 does not match the MEC 1918. In such cases, the algorithm delivers a "FALSE" value and prepares a report warning the analyst about a potential fraud 1920, and no further analysis of the sample is performed.

Figure 18:
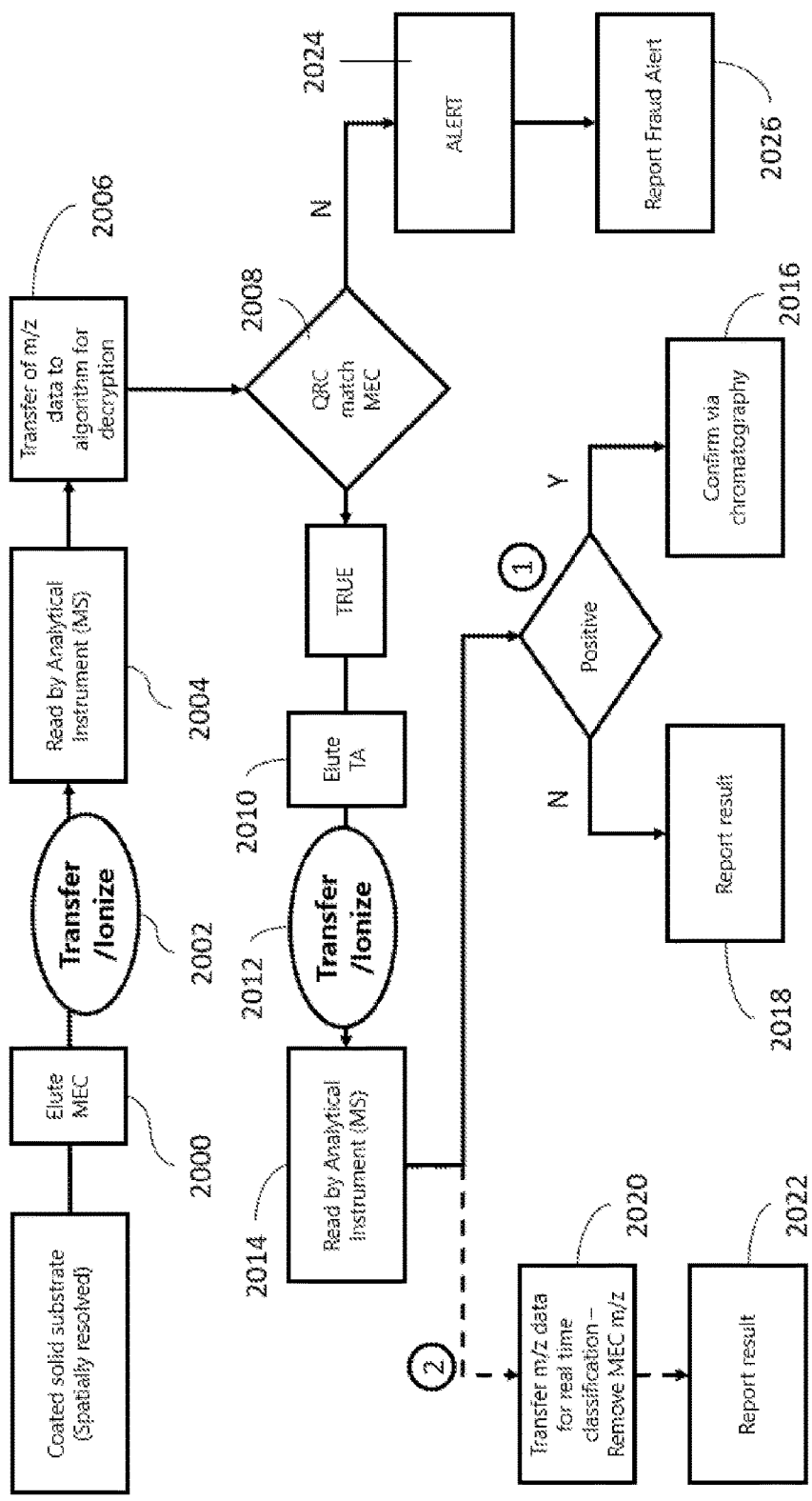
FIG. 18 illustrates a workflow for deciphering molecular information on molecular cryptographic sampling devices when there is spatial resolution of the target analyte and the molecular tag and the elution is executed with temporal resolution, for instance using a liquid extraction surface analysis or a multi-liquid micro junction system, according to an embodiment of the present disclosure.

FIG. 18 illustrates the workflow for deciphering molecular information on molecular cryptographic sampling devices 10 when the TA and the MT are spatially resolved and the elution is executed with temporal resolution, for instance using a LESA or a multi-LMJ system. First, the MEC is discretely eluted from the molecular cryptographic sampling device 10, 2000 and transferred to the analytical instrument 2002. The MEC is read by the analytical instrument, preferably a mass spectrometer 2004. Then, the data is transferred to an algorithm 2006 for decryption. If the information on the indicia placed on the molecular cryptographic sampling device 2010 matches the MEC 2008 stored on the molecular cryptographic sampling device 10, it is confirmed the identity of the sample/device and the algorithm reports a "TRUE" value which allows for further examination of the TA deposited on a different loading zone. Then, the TA(s) are discretely eluted from the molecular cryptographic sampling device 2010 and transferred to the analytical instrument 2012. The TAs are read by the analytical instrument, preferably a mass spectrometer 2014. In one example, if there is a quantitative process and the result is positive and above the limits of quantitation of the method, the algorithm would suggest the analyst confirm via a separation technology such as liquid chromatography 2016. If there is a quantitative process and the result is negative, the algorithm would suggest to report the results and continue with the following sample 2018. Alternatively, if the molecular cryptographic sampling device 10 is used for a qualitative assessment of the sample (e.g., molecular profiling), the algorithm transfers the sample data to a separate algorithm for real-time classification 2020. Based on a data base previously build by the analyst, the classification algorithm 2022 determines the potential identity of the sample under scrutiny. In one example, exemplified in FIG. 18, the information on the indicia placed on the molecular cryptographic sampling device 2010 does not match the MEC 2024. In such cases, the algorithm delivers a "FALSE" value and prepares a report warning the analyst about a potential fraud 2026, and no further analysis of the sample is performed.

Figure 19:
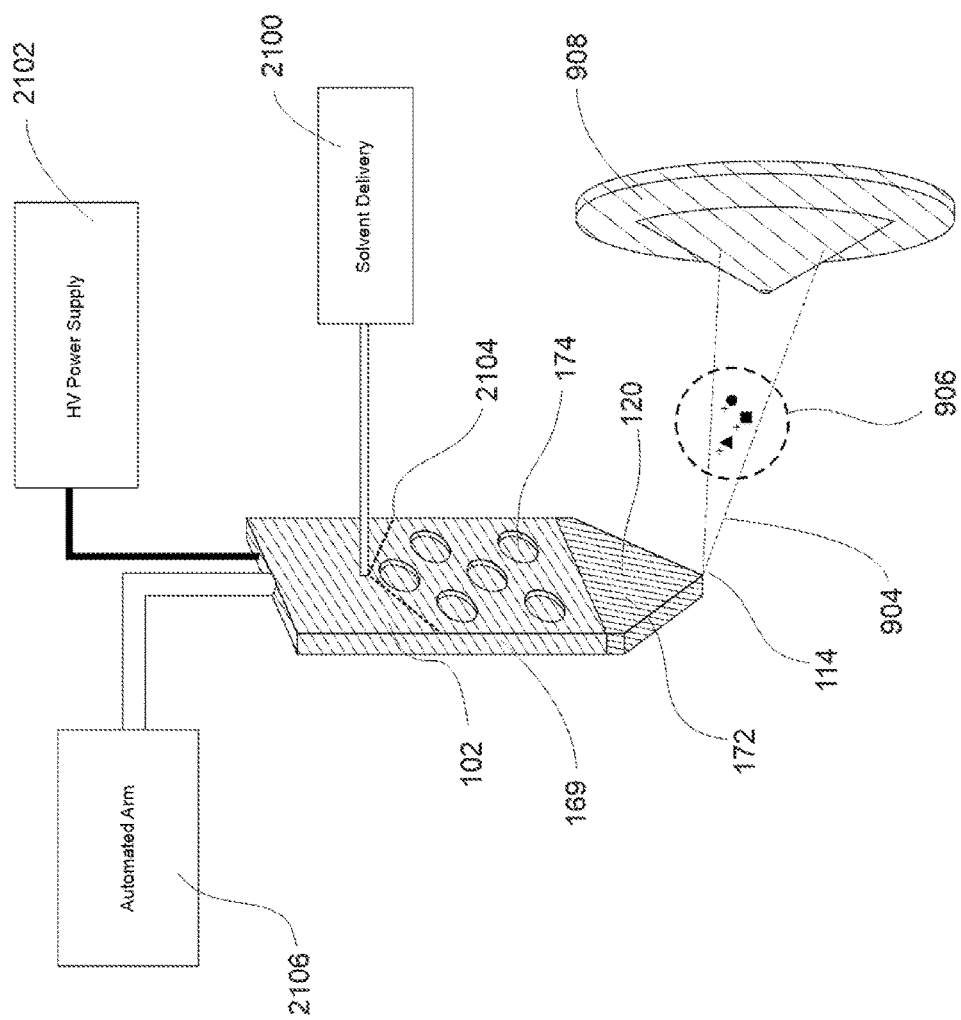
FIG. 19 illustrates the usage of a molecular cryptographic sampling device for orthogonal substrate electrospray ionization, according to an embodiment of the present disclosure.

FIG. 19 illustrates the usage of a molecular cryptographic sampling device 10, 169 for orthogonal substrate electrospray ionization that expels ions orthogonally in regard to the MS inlet. Essentially, a robotic arm 2106 presents the molecular cryptographic sampling device 10, 169 in front of the MS inlet 908. Then, a solvent delivery system 2100 releases a finite amount of elution solvent 2104 on the upper part 174 (i.e., non-sharp edge of the substrate 102) of the molecular cryptographic sampling device 10, 169. The geometry on the upper part of the molecular cryptographic sampling device 10, 169 facilitates the collection of elution solvent and controlled release of the elution solvent onto the loading zone of the TA and MT 172. After a fixed interaction time (e.g., 10 seconds), a high-voltage supply 2102 is applied to the molecular cryptographic sampling device 10, 169 and an electrospray Taylor cone 904 is generated at the tip 114 of the substrate 102. Ions 906 are expelled from the molecular cryptographic sampling device 10, 169 and transferred to the MS inlet 908 for analysis. In preferred examples, the mass spectrometry system is a time of flight MS which allows obtaining high resolution mass spectrometry data 2108. Other high-end mass spectrometry systems may also be used to obtain further information including, but not limited to, triple quadrupole, orbitrap, quadrupole time of flight, and ion cyclotron. Likewise, a person skilled in the art would comprehend that other ion separation technologies, such ion mobility analyzers, would further enhance the selectivity by adding additional information (i.e., drift time) about the TA and MEC. Examples of ion mobility analyzers include the following: differential mobility (DMS), trapped ion mobility spectrometry (TIMS), travel wave ion mobility (TWIMS), structural for lossless ion manipulations (SLIM), drift tube, and high-field asymmetric waveform ion mobility spectrometry (FAIMS).

Figure 20:
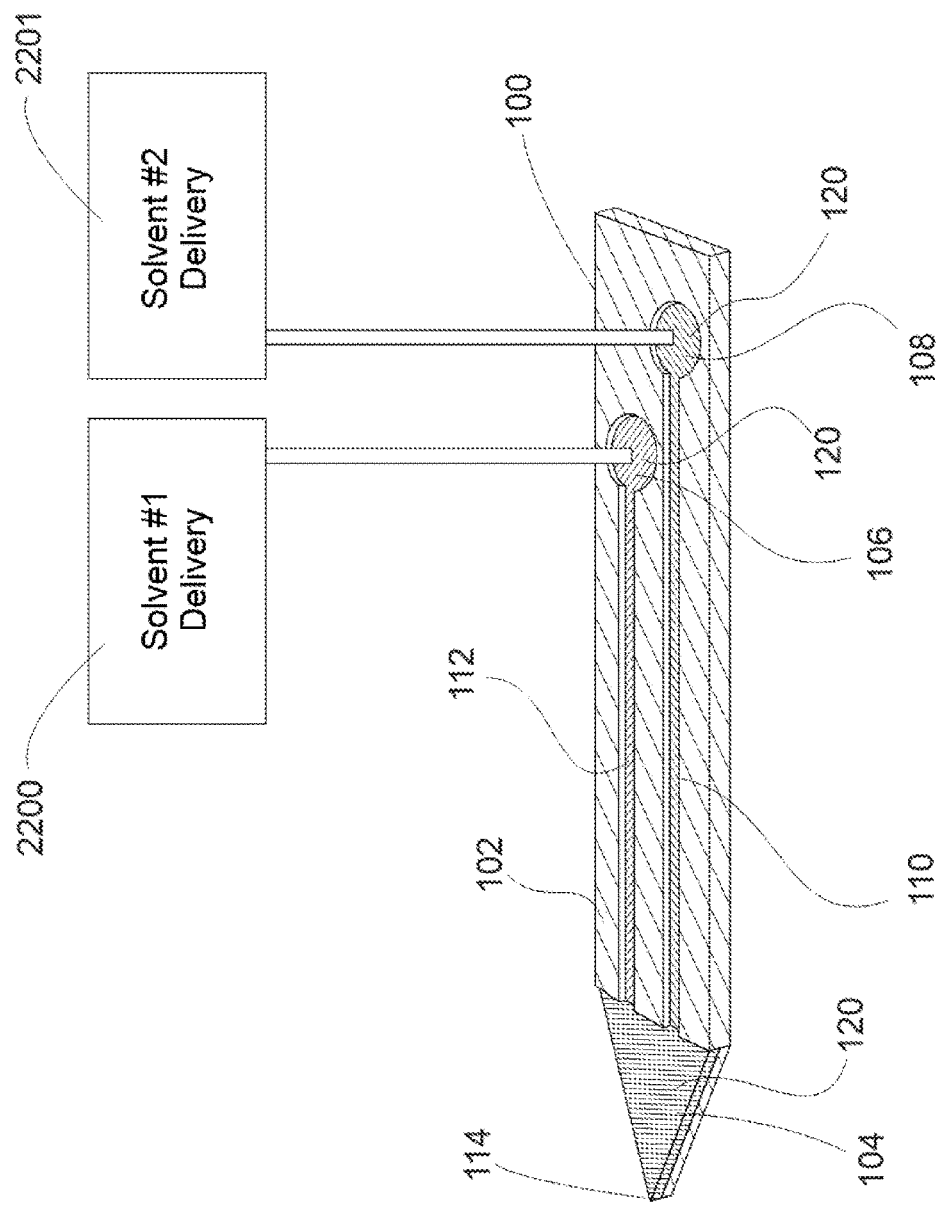
FIG. 20 exemplifies a mechanism to deposit molecular calibrant, ID tag, molecular reactive tag, and any other molecular tag on the surface of a substrate of a molecular cryptographic sampling device, and in specific loading zones, according to an embodiment of the present disclosure.

FIG. 20. Exemplifies a mechanism to deposit MC, IDT, MRT, and any other MT on the surface of the substrate 102. In preferred examples, MTs are loaded in diverse loading zones 106 and 108 which are spatially resolved on the molecular cryptographic sampling device 10. In a particular experiment, a set of at least two solvent delivery systems 2200 and 2201 are mounted on a XYZ robotic arm to selectively release the MT on either the indentations or the protrusions 104, 106, 108 of the molecular cryptographic sampling device 10. In other examples, where the solvent delivery system is a sprayer, it may be mildly heated to provide better desolvation of the droplets containing the MT and the MEC and more homogenous application of the MT on the area of interest. After application, the solvent containing the MT is let to evaporate and the molecular cryptographic sampling devices 10 are stored under inert conditions until its final use.

Figure 21:
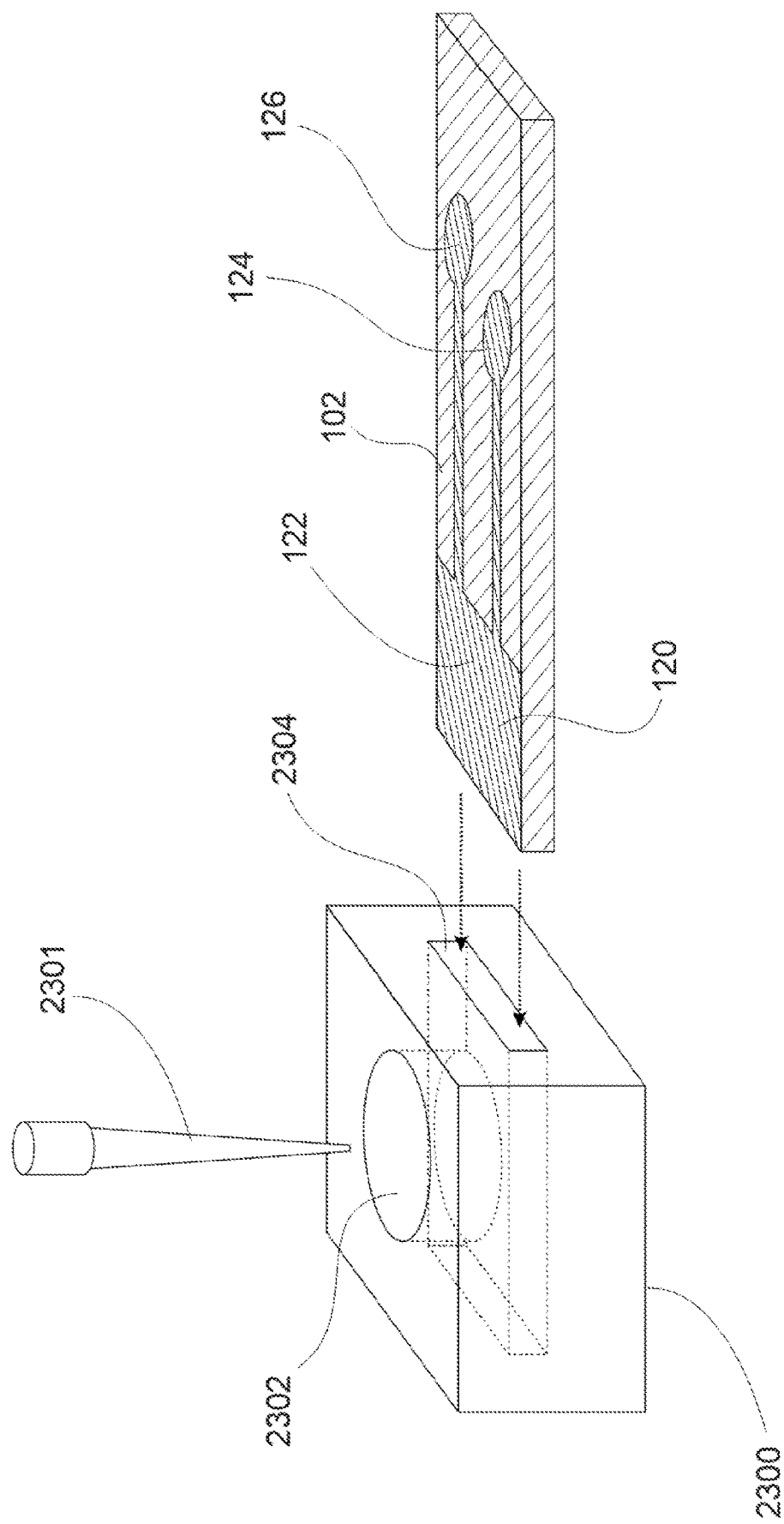
FIG. 21 illustrates the coupling of a molecular cryptographic sampling device interface with a micro sampling device for biofluids, according to an embodiment of the present disclosure.

FIG. 21. Illustrates the coupling of the molecular cryptographic sampling device 10 interface with a sampling device that collects minute amounts of biofluids 2300. The biological sample is delivered using a sample dispensing device 2301 to a sampled collecting port 2302. By gravity, the sample is transported to a sampling chamber 2304 on the device 2300 where the molecular cryptographic sampling device 10 was previously inserted. Only the TA loading zone 122 is exposed to the biological fluid for a fixed period of time. The loading zones 124, 126 are used exclusively to store MT such as IDT, MC, and MRT. After the analyte collection is completed, the loading zone 122 is rinsed with water to remove any potential matrix components attached to the sorbent. Subsequently, the device is dried and either stored in a freezer, transported to a laboratory for analysis, or analyzed immediately. The sample under scrutiny exclusively interacts with the TA loading zone.

While the foregoing specification illustrates and describes exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A molecular cryptographic sampling device, comprising:
   at least one unique identifying indicia disposed on the molecular cryptographic sampling device;
   a substrate including at least one depression disposed in or protrusion disposed on a surface of the substrate;
   at least one polymeric sorbent coating disposed on the at least one depression or protrusion; and at least one molecular encrypted code disposed on the at least one polymeric sorbent coating, the at least one molecular encrypted code including at least one molecular tag, wherein the at least one molecular encrypted code is uniquely associated with the at least one unique identifying indicia in a database or by a predetermined algorithm, and wherein the at least one molecular encrypted code includes at least one molecular reactive tag having a known reaction with a target analyte or a second molecular tag, such that in the presence of the target analyte or the second molecular tag, the molecular reactive tag reacts with the target analyte, the second molecular tag, or both of the target analyte and the second molecular tag to form a molecularly encoded product.

2. The molecular cryptographic sampling device of claim 1, wherein the molecular cryptographic sampling device is a mass spectrometry electrospray device.

3. The molecular cryptographic sampling device of claim 2, wherein the molecular cryptographic sampling device is arranged and configured to collect an analyte, enrich the analyte, transport the analyte, and ionize the analyte.

4. The molecular cryptographic sampling device of claim 1, wherein the at least one polymeric sorbent coating is distributed heterogeneously on the substrate.

5. A molecular cryptographic sampling device, comprising:
   at least one unique identifying indicia disposed on the molecular cryptographic sampling device;
   a substrate including at least one depression disposed in or protrusion disposed on a surface of the substrate;
   at least one polymeric sorbent coating disposed on the at least one depression or protrusion; and
   at least one molecular encrypted code disposed on the at least one polymeric sorbent coating, the at least one molecular encrypted code including at least one molecular tag,
   wherein the at least one molecular encrypted code is uniquely associated with the at least one unique identifying indicia in a database or by a predetermined algorithm, and
   wherein the at least one polymeric sorbent coating includes at least two different types of polymeric material on each face of the molecular cryptographic sampling device, and the at least one polymeric sorbent coating is disposed on each face of the molecular cryptographic sampling device.

6. A molecular cryptographic sampling device, comprising:
   at least one unique identifying indicia disposed on the molecular cryptographic sampling device;
   a substrate including at least one depression disposed in or protrusion disposed on a surface of the substrate;
   at least one polymeric sorbent coating disposed on the at least one depression or protrusion; and
   at least one molecular encrypted code disposed on the at least one polymeric sorbent coating, the at least one molecular encrypted code including at least one molecular tag,
   wherein the at least one molecular encrypted code is uniquely associated with the at least one unique identifying indicia in a database or by a predetermined algorithm, and
   wherein the molecular cryptographic sampling device includes a predetermined pattern of at least one of holes and grooves arranged and configured for accumulation of elution solvent and controlled release of the elution solvent onto to the at least one polymeric sorbent coating while the molecular cryptographic sampling device is an orthogonal to mass spectrometer electrospray ionization inlet.

7. The molecular cryptographic sampling device of claim 1, wherein the at least one molecular encrypted code includes a plurality of the at least one molecular tag, and the molecular encrypted code is defined by at least one of the number of molecular tags in the plurality of the at least one molecular tag, the amount of each molecular tag of the plurality of the at least one molecular tag, or the ratio of molecular tags of the plurality of the at least one molecular tag.

8. The molecular cryptographic sampling device of claim 1, wherein the at least one molecular encrypted code includes at least one molecular internal standard, the molecular internal standard including an isotopically labelled analogue of a target analyte.

9. A method for encoding a molecular cryptographic sampling device, comprising:
   determining via a predetermined algorithm a molecular encrypted code to be imprinted on the molecular cryptographic sampling device wherein the at least one molecular encrypted code is uniquely associated with at least one unique identifying indicia by the predetermined algorithm, the molecular cryptographic sampling device including:
      a substrate including at least one depression disposed in or protrusion disposed on a surface of the substrate; and
      at least one polymeric sorbent coating disposed on the at least one depression or protrusion;
   transferring molecular encrypted code information to a fluidic system;
   mixing one or more molecular tags by the fluidic system in response to the molecular encrypted code information to form the at least one molecular encrypted code;
   disposing the at least one molecular encrypted code on the at least one polymeric sorbent coating, the at least one molecular encrypted code including the at least one molecular tag; and
   disposing the at least one unique identifying indicia on the molecular cryptographic sampling device.

10. A method for validating a molecular cryptographic sampling device, comprising:
    associating the molecular cryptographic sampling device with an analytical instrument, the molecular cryptographic sampling device comprising:
       at least one unique identifying indicia disposed on the molecular cryptographic sampling device;
       a substrate including at least one depression disposed in or protrusion disposed on a surface of the substrate;
       at least one polymeric sorbent coating disposed on the at least one depression or protrusion; and
       at least one molecular encrypted code disposed on the at least one polymeric sorbent coating, the at least one molecular encrypted code including at least one molecular tag,
       wherein the at least one molecular encrypted code is uniquely associated with the at least one unique identifying indicia in a database or by a predetermined algorithm;
    eluting the at least one molecular tag of the at least one molecular encrypted code from the molecular cryptographic sampling device;

transferring the at least one molecular tag of the at least one molecular encrypted code to the analytical instrument;

analyzing the at least one molecular tag of the at least one molecular encrypted code with the analytical instrument;

reading the at least one unique identifying indicia;

comparing the at least one molecular tag of the at least one molecular encrypted code with the at least one unique identifying indicia via the database or the predetermined algorithm; and returning a positive value if the at least one molecular tag of the at least one molecular encrypted code corresponds to the at least one unique identifying indicia or a negative value if the at least one molecular encrypted code does not correspond with the at least one unique identifying indicia.

11. The method of claim 10, further including eluting a target analyte from the molecular cryptographic sampling device.

12. The method of claim 11, wherein eluting the target analyte from the molecular cryptographic sampling device is simultaneous with eluting the at least one molecular tag of the at least one molecular encrypted code.

13. The method of claim 12, wherein the at least one target analyte is only analyzed only after the positive value is returned.

14. The method of claim 12, wherein the at least one target analyte is analyzed simultaneously with the at least one molecular tag of the at least one molecular encrypted code, and analysis of the at least one target analyte is reported only after the positive value is returned.

15. The method of claim 11, wherein eluting the target analyte from the molecular cryptographic sampling device occurs only after the positive value is returned.

16. The molecular cryptographic sampling device of claim 5, wherein the molecular cryptographic sampling device is a mass spectrometry electrospray device and the molecular cryptographic sampling device is arranged and configured to collect an analyte, enrich the analyte, transport the analyte, and ionize the analyte.

17. The molecular cryptographic sampling device of claim 5, wherein the at least one molecular encrypted code includes a plurality of the at least one molecular tag, and the molecular encrypted code is defined by at least one of the number of molecular tags in the plurality of the at least one molecular tag, the amount of each molecular tag of the plurality of the at least one molecular tag, or the ratio of molecular tags of the plurality of the at least one molecular tag.

18. The molecular cryptographic sampling device of claim 5, wherein the at least one molecular encrypted code includes at least one molecular internal standard, the molecular internal standard including an isotopically labelled analogue of a target analyte.

19. The molecular cryptographic sampling device of claim 6, wherein the molecular cryptographic sampling device is a mass spectrometry electrospray device and the molecular cryptographic sampling device is arranged and configured to collect an analyte, enrich the analyte, transport the analyte, and ionize the analyte.

20. The molecular cryptographic sampling device of claim 6, wherein the at least one molecular encrypted code includes at least one of:
   a plurality of the at least one molecular tag, the molecular encrypted code being defined by at least one of the number of molecular tags in the plurality of the at least one molecular tag, the amount of each molecular tag of the plurality of the at least one molecular tag, or the ratio of molecular tags of the plurality of the at least one molecular tag; or
   at least one molecular internal standard, the molecular internal standard including an isotopically labelled analogue of a target analyte.

* * * * *